(12) United States Patent
Rapoport

(10) Patent No.: US 9,974,705 B2
(45) Date of Patent: May 22, 2018

(54) FOAMED PATIENT TRANSPORT INCUBATOR

(71) Applicant: Aspect Imaging Ltd., Shoham (IL)

(72) Inventor: Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 383 days.

(21) Appl. No.: 14/531,289

(22) Filed: Nov. 3, 2014

(65) Prior Publication Data

US 2015/0126804 A1    May 7, 2015

Related U.S. Application Data

(60) Provisional application No. 61/899,233, filed on Nov. 3, 2013.

(30) Foreign Application Priority Data

Nov. 4, 2013   (DE) .................... 20 2013 104 934 U

(51) Int. Cl.
  *A61G 11/00* (2006.01)
  *A61B 5/055* (2006.01)
  (Continued)

(52) U.S. Cl.
  CPC ............ *A61G 11/00* (2013.01); *A61B 5/0555* (2013.01); *A61G 10/00* (2013.01); *A61G 10/02* (2013.01);
  (Continued)

(58) Field of Classification Search
  CPC ...... A61G 10/00; A61G 10/02; A61G 11/009; A61G 2210/00; A61G 2210/90;
  (Continued)

(56) References Cited

U.S. PATENT DOCUMENTS

| 1,900,342 A | 3/1933 | Hess |
| 2,638,087 A | 5/1953 | Livsey |

(Continued)

FOREIGN PATENT DOCUMENTS

| CA | 2815746 | 5/2012 |
| CN | 2448344 | 9/2001 |

(Continued)

OTHER PUBLICATIONS

Thermaxx Jackets, 5 Most Common Thermal Insulation Materials by Thermaxx Jackets, Jun. 28, 2011, pp. 1-3.*

(Continued)

*Primary Examiner* — Navin Natnithithadha
*Assistant Examiner* — Sunita Reddy
(74) *Attorney, Agent, or Firm* — Pearl Cohen Zedek Latzer Baratz LLP

(57) ABSTRACT

A patient transport incubator (PTI) suitable for MRI device having an open bore; the PTI comprises an inner volume having a first set of dimensions, adapted by means of shape and size to accommodate a patient or accommodate at least a portion of an MRI-compatible neonate's cradle, the inner volume is further covered by an envelope having a second set of dimensions, adapted by means of shape and size to be temporarily introduced within the open bore; wherein at least a portion of the envelope comprises MRI safe thermo-isolating and noise reducing foam. The invention will increase the safety and comfort of MRI scanning of neonates.

11 Claims, 7 Drawing Sheets

(51) Int. Cl.
*A61G 10/00* (2006.01)
*A61G 10/02* (2006.01)
(52) U.S. Cl.
CPC ........ *A61G 11/009* (2013.01); *A61G 2203/70* (2013.01); *A61G 2210/00* (2013.01); *A61G 2210/50* (2013.01); *A61G 2210/90* (2013.01)
(58) Field of Classification Search
CPC ................ A61G 11/00; A61G 2203/70; A61G 2210/50; A61B 5/0555
USPC ..................................................... 600/21, 22
See application file for complete search history.

(56) References Cited

U.S. PATENT DOCUMENTS

| | | | |
|---|---|---|---|
| 2,708,927 | A | 5/1955 | Dixon et al. |
| 3,012,836 | A | 12/1961 | Smith et al. |
| 3,315,671 | A | 4/1967 | Creelman |
| 3,470,866 | A | 10/1969 | Gittelson |
| 3,655,178 | A | 4/1972 | Vezina |
| 3,710,791 | A | 1/1973 | Deaton |
| 3,920,000 | A | 11/1975 | Atherton et al. |
| 4,161,172 | A | 7/1979 | Pickering |
| 4,509,505 | A | 4/1985 | Mercey et al. |
| 4,712,263 | A | 12/1987 | Pronzinski |
| 4,750,474 | A | 6/1988 | Dukhan et al. |
| 4,936,824 | A | 6/1990 | Koch et al. |
| 5,059,906 | A | 10/1991 | Yamanaka |
| 5,100,375 | A | 3/1992 | Koch |
| 5,446,934 | A | 9/1995 | Frazier |
| 5,534,669 | A | 7/1996 | Schroeder et al. |
| 5,759,149 | A | 6/1998 | Goldberg et al. |
| 5,797,833 | A | 8/1998 | Kobayashi et al. |
| 5,800,335 | A | 9/1998 | Koch et al. |
| 5,817,003 | A | 10/1998 | Moll et al. |
| 5,943,716 | A | 8/1999 | Chu |
| 5,971,913 | A | 10/1999 | Newkirk et al. |
| 6,036,634 | A | 3/2000 | Goldberg et al. |
| 6,155,970 | A | 12/2000 | Dykes et al. |
| 6,231,499 | B1 | 5/2001 | Jones |
| D446,675 | S | 8/2001 | Straub |
| 6,317,618 | B1 | 11/2001 | Livni et al. |
| 6,409,654 | B1 | 6/2002 | McClain et al. |
| 6,433,548 | B1 | 8/2002 | Furuta et al. |
| 6,471,634 | B1 | 10/2002 | Dykes et al. |
| 6,511,414 | B1 | 1/2003 | Hamsund |
| 6,611,702 | B2 | 8/2003 | Rohling et al. |
| 6,641,521 | B2 | 11/2003 | Kolarovic |
| 6,666,816 | B2 | 12/2003 | Mountain |
| RE38,453 | E | 3/2004 | Lessard et al. |
| 6,860,272 | B2 | 3/2005 | Carter et al. |
| 6,882,878 | B2 | 4/2005 | Schmit et al. |
| 6,992,486 | B2 * | 1/2006 | Srinivasan ....... G01R 33/34046 324/309 |
| 7,255,671 | B2 | 8/2007 | Boone et al. |
| 7,278,962 | B2 | 10/2007 | Lonneker-Lammers |
| D567,948 | S | 4/2008 | Tierney et al. |
| 7,482,558 | B2 | 1/2009 | Koch |
| 7,599,728 | B2 | 10/2009 | Feenan |
| 7,784,121 | B2 | 8/2010 | Ahlman |
| 8,147,396 | B2 | 4/2012 | Srinivasan |
| 8,851,018 | B2 | 10/2014 | Rapoport et al. |
| 8,896,310 | B2 | 11/2014 | Rapoport |
| 2001/0049465 | A1 | 12/2001 | Goldberg et al. |
| 2002/0072648 | A1 | 6/2002 | Dykes et al. |
| 2002/0123681 | A1 | 9/2002 | Zuk et al. |
| 2002/0143233 | A1 | 10/2002 | Donnelly et al. |
| 2002/0173696 | A1 | 11/2002 | Kolarovic et al. |
| 2002/0173717 | A1 | 11/2002 | Rohling et al. |
| 2004/0030241 | A1 | 2/2004 | Green et al. |
| 2004/0034273 | A1 | 2/2004 | Boris |
| 2004/0133064 | A1 | 7/2004 | Castillon et al. |
| 2004/0186341 | A1 | 9/2004 | McDermott |
| 2004/0236174 | A1 * | 11/2004 | Boone .................. A61G 11/006 600/21 |
| 2004/0236175 | A1 | 11/2004 | Boone et al. |
| 2005/0004422 | A1 | 1/2005 | Caspary et al. |
| 2005/0020906 | A1 | 1/2005 | Seijger et al. |
| 2005/0038314 | A1 | 2/2005 | Falk |
| 2005/0113668 | A1 | 5/2005 | Srinivasan |
| 2006/0079730 | A1 | 4/2006 | Getsla |
| 2007/0232894 | A1 | 10/2007 | Feenan |
| 2008/0163425 | A1 * | 7/2008 | White .................. A61G 7/0503 5/603 |
| 2010/0004502 | A1 | 1/2010 | Honma et al. |
| 2010/0168502 | A1 | 7/2010 | Delaporte et al. |
| 2011/0048424 | A1 | 3/2011 | Radko |
| 2011/0162652 | A1 | 3/2011 | Rapoport |
| 2011/0186049 | A1 | 3/2011 | Rapoport |
| 2011/0113555 | A1 | 5/2011 | Smith |
| 2011/0125010 | A1 | 5/2011 | Vaquero et al. |
| 2011/0160521 | A1 | 6/2011 | Khodak et al. |
| 2011/0234347 | A1 | 9/2011 | Rapoport |
| 2011/0304333 | A1 | 12/2011 | Rapoport |
| 2012/0071745 | A1 | 3/2012 | Rapoport |
| 2012/0073511 | A1 | 3/2012 | Rapoport et al. |
| 2012/0077707 | A1 | 3/2012 | Rapoport |
| 2012/0119742 | A1 | 5/2012 | Rapoport |
| 2012/0126814 | A1 | 5/2012 | Fischer et al. |
| 2013/0079624 | A1 | 3/2013 | Rapoport |
| 2013/0109956 | A1 | 5/2013 | Rapoport |
| 2013/0237803 | A1 | 5/2013 | Rapoport |
| 2013/0150656 | A1 | 6/2013 | Falk et al. |
| 2013/0204074 | A1 | 8/2013 | Belval et al. |
| 2013/0204617 | A1 | 8/2013 | Kuo et al. |
| 2013/0328559 | A1 | 12/2013 | Rapoport |
| 2013/0328560 | A1 | 12/2013 | Rapoport |
| 2013/0328563 | A1 | 12/2013 | Rapoport |
| 2013/0334439 | A1 | 12/2013 | Etters |
| 2014/0003614 | A1 | 1/2014 | Levitov et al. |
| 2014/0050827 | A1 | 2/2014 | Rapoport |
| 2014/0051973 | A1 | 2/2014 | Rapoport et al. |
| 2014/0051974 | A1 | 2/2014 | Rapoport et al. |
| 2014/0051976 | A1 | 2/2014 | Rapoport et al. |
| 2014/0098934 | A1 | 4/2014 | Kondo |
| 2014/0099010 | A1 | 4/2014 | Rapoport |
| 2014/0103927 | A1 | 4/2014 | Rapoport |
| 2014/0117989 | A1 | 5/2014 | Rapoport |
| 2014/0128725 | A1 | 5/2014 | Rapoport |
| 2014/0139216 | A1 | 5/2014 | Rapoport |
| 2014/0142914 | A1 | 5/2014 | Rapoport |
| 2014/0152302 | A1 | 6/2014 | Rapoport et al. |
| 2014/0152310 | A1 | 6/2014 | Rapoport |
| 2014/0158062 | A1 | 6/2014 | Rapoport et al. |
| 2014/0230850 | A1 | 8/2014 | Rapoport |
| 2014/0257081 | A1 | 9/2014 | Rapoport |
| 2014/0266203 | A1 | 9/2014 | Rapoport |
| 2014/0300358 | A1 | 10/2014 | Rapoport |
| 2014/0357981 | A1 | 12/2014 | Dumoulin |
| 2014/0364722 | A1 | 12/2014 | Dumoulin |
| 2014/0378821 | A1 | 12/2014 | Rapoport et al. |
| 2014/0378825 | A1 | 12/2014 | Rapoport et al. |
| 2015/0065788 | A1 | 3/2015 | Rapoport |
| 2015/0137812 | A1 | 5/2015 | Rapoport |
| 2015/0141799 | A1 | 5/2015 | Rapoport et al. |
| 2016/0030264 | A1 | 2/2016 | Lehmann et al. |
| 2016/0081582 | A1 | 3/2016 | Rapoport |

FOREIGN PATENT DOCUMENTS

| | | |
|---|---|---|
| CN | 102551719 A | 7/2012 |
| DE | 19617739 | 6/1997 |
| EP | 1132072 | 9/2001 |
| EP | 2581071 | 4/2013 |
| IL | 226488 A | 5/2013 |
| JP | 2007252741 | 10/2007 |
| JP | 2010178857 | 8/2010 |
| WO | WO1998048756 | 11/1998 |
| WO | WO9921526 | 5/1999 |
| WO | 2008137003 A1 | 11/2008 |
| WO | WO2008137003 | 11/2008 |
| WO | WO2010054457 | 5/2010 |

(56) References Cited

FOREIGN PATENT DOCUMENTS

| WO | WO2011109761 | 9/2011 |
|---|---|---|
| WO | WO2012143825 | 10/2012 |
| WO | WO2013115847 | 8/2013 |

OTHER PUBLICATIONS

U.S. Appl. No. 61/893,959, filed Oct. 22, 2013, Rapoport, Uri.
International Search Report of PCT Application No. PCT/IL2014/50948, dated May 20, 2015.
The Association for the Advancement of Medical Instrumentation, ANSI/AAMI/IEC 60601-2-20:2009, Medical Electrical Equipment, Part 2-20, Particular Requirements for the Basic Safety and Essential Performance of Infant Transport Incubators, Feb. 20, 2009, Sections 201.3.201 through 201.3.210, The Association for the Advancement of Medical Instrumentation, Arlington, VA, USA.
Aspect Imaging Ltd., "Shutting Assembly for Closing an Entrance of an MRI Device", co-pending U.S. Appl. No. 14/540,163, filed Nov. 13, 2014.
Aspect Imaging Ltd, "MRI—Incubator's Closure Assembly", co-pending U.S. Appl. No. 14/539,442, filed Nov. 12, 2014.
Aspect Imaging Ltd., "Cage in an MRD with a Fastening/Attenuating System", co-pending U.S. Appl. No. 14/527,950, filed Oct. 30, 2014.
Rapoport, Uri, "RF Shielding Conduit in an MRI Closure Assembly", co-pending U.S. Appl. No. 14/574,785, filed Dec. 18, 2014.
Aspect Imaging Ltd., "System and Method for Generating Invasively Hyperpolarized Images", co-pending U.S. Appl. No. 14/556,682, filed Dec. 1, 2014.
Aspect Imaging Ltd., "System and Method for Generating Invasively Hyperpolarized Images", co-pending U.S. Appl. No. 14/556,654, filed Dec. 1, 2014.
Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.
Aspect Imaging Ltd., "Chamber for Housing Animals During Anaesthetic Procedures", co-pending U.S. Appl. No. 14/537,266, filed Nov. 10, 2014.
Aspect Imaging Ltd., "RF Automated Tuning System Used in a Magnetic Resonance Device and Methods Thereof", co-pending U.S. Appl. No. 14/588,741, filed Jan. 2, 2015.
Aspect Imaging Ltd., "Means for Operating an MRI Device Within a RF-Magnetic Environment", co-pending U.S. Appl. No. 14/596,320, filed Jan. 14, 2015.
Aspect Imaging Ltd., "Means and Method for Operating an MRI Device Within a RF-Magnetic Environment", co-pending U.S. Appl. No. 14/596,329, filed Jan. 14, 2015.
Aspect Imaging Ltd., "CT/MRI Integrated System for the Diagnosis of Acute Strokes and Methods Thereof", co-pending U.S. Appl. No. 14/598,517, filed Jan. 16, 2015.
Aspect Imaging Ltd., "Mechanical Clutch for MRI", co-pending U.S. Appl. No. 14/611,379, filed Feb. 2, 2015.
Aspect Imaging Ltd., "Method for Providing High Resolution, High Contrast Fused MRI Images", co-pending U.S. Appl. No. 13/877,533, filed May 22, 2014.
Aspect Imaging Ltd., "Method for Manipulating the MRI's Protocol of Pulse-Sequences", co-pending U.S. Appl. No. 14/070,695, filed Nov. 4, 2013.
Aspect Imaging Ltd., "Foamed Patient Transport Incubator", co-pending U.S. Appl. No. 14/531,289, filed Nov. 3, 2014.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Antonucci, et al., The infant incubator in the neonatal intensive care unit: unresolved issues and future developments, J. Perinat. Med. 37(2009), 587-598.
Baby Pod II Infant Transport Device, Advance Healthcare Technology, brochure, pp. 1-6.
Baby Pod II Operation and Maintenance Manual, revision 5, Jan. 2011, pp. 1-11.
Ferris et al., The design of neonatal incubators: a systems-oriented, human centered approach, J. Perinatology, 2013, 33, S24-S31.
Kim et al., Air transparent soundproof window, AIP Advances 4, 117123 (2014), published online, doi: http://dx.doi.org/10.1069/1.4902155.
Knutson, Allysa Jennie, Acceptable noise levels for neonates in the neonatal intensive care unit, A Capstone Project submitted in partial fulfillment of the requirements for the degree of: Doctor of Audiology, Washington University School of Medicine Program in Audiology and Communication Sciences, May 17, 2013, pp. 1-59.
Liu, Lichuan et al., Development and Applications of Active Noise Control System for Infant Incubators, Proceedings of the 2009 IEEE International Conference on Systems, Man, and Cybernetics San Antonio, TX, USA—Oct. 2009, pp. 1-6.
Mahil et al., Hybrid Swarm Algorithm for the Suppression of Incubator Interference in Premature Infants ECG, Research Journal of Applied Sciences, Engineering and Technology 6(16): 2931-2935, 2013.
Marik et al., Neonatal incubators: A toxic sound environment for the preterm infant?, Pediatr Crit Care Med 2012 vol. 13, No. 6. pp. 1-6.
Paley et al., An MR-compatible neonatal incubator, The British Journal of Radiology, 85, 2012, 952-958.
American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.
Ranganna et al., Reducing noise on the neonatal unit, Infant, 2011, vol. 7, Issue 1, pp. 25-28.
Jenkins, S., ScanPod, BabyPod-Products-ScanPod, 2002-2011 Advance Healthcare Technology, ltd., internet website http://babypod.com:80/products/scanpod.php.
Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-inside_the_preemie_brain.htm.
Kitterman et al., Catheterization of umbilical vessels in newborn infants, Pediatric Clinics of North America, vol. 17, No. 4, Nov. 1970, 895-912.

* cited by examiner

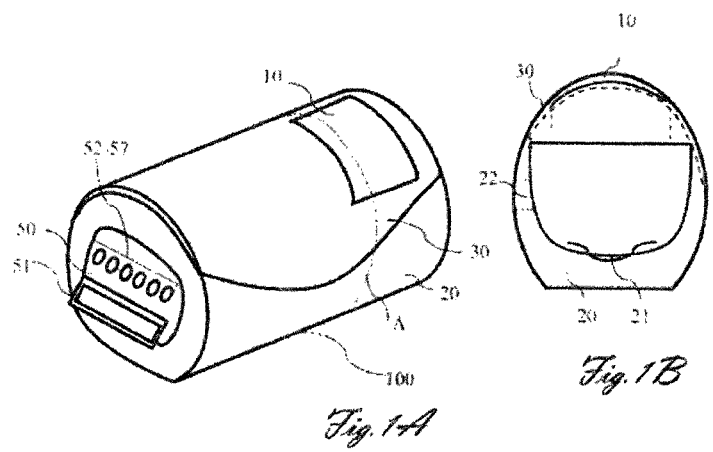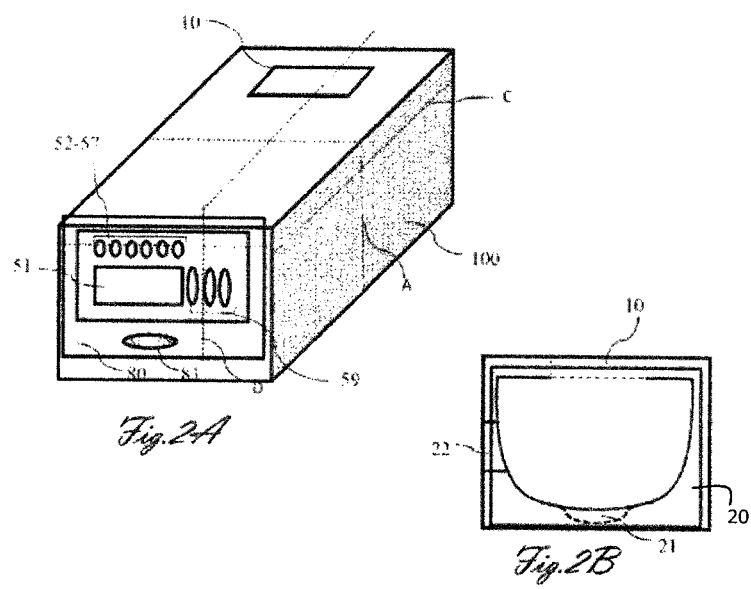

FOAMED PATIENT TRANSPORT INCUBATOR

CROSS REFERENCE TO RELATED APPLICATIONS

This application claims the benefit of and priority to U.S. Application Ser. No. 61/893,959, filed on Nov. 13, 2013, the entire contents of which are incorporate herein by reference in its entirety.

FIELD OF THE INVENTION

The present invention relates to equipment for MRI imaging of patients. In particular, the present invention pertains to providing an MRI safe patient transport incubator, with the technological means to maintain thermo-isolation, noise reduction and welfare of patients during MRI, and a standard of care protocol for maintaining patient thermoregulation.

BACKGROUND OF THE INVENTION

MRI technology is frequently used to diagnose patient health and for research purposes. During MRI, patients experience bodily temperature change, and exposure to high levels of noise up to 120 dB and stress (as described in Wikipedia "MRI").

These predicaments are especially problematic when submitting neonates to MRI. Newborn infants and specifically those born prematurely require attentive care. They are kept in a stable environment where the temperature, humidity and gas levels are constantly monitored, while many times connected to life support equipment. Neonates are especially liable to infections and therefore sterile and/or disposable gear is usually used when handling them.

During MRI of a patient, there is a need to maintain environment conditions and minimize stress while allowing monitoring of the patient's health. Many factors contribute to the successful and quick completion of an MRI. Among these factors, minimizing movements of the patient during MRI will result in better quality imaging, consequently leading to less repetitions of the imaging process. Patients experiencing a drop in body temperature will respond by moving in an attempt to keep warm. Infants are especially sensitive to a drop in body temperature which can also lead to health complications such as hypothermia, affecting their cardio and respiratory systems.

WO 2008/137003 describes an acoustic noise attenuation system for MRI scanning. This system comprises a capsule having two ends and configured both to enclose the entire body of a subject undergoing a scanning procedure in an MRI scanner having an inner bore and to fit within the scanner bore. At least one end of the enclosure is fitted with acoustically sealed pathways or connectors for monitoring or communicating with the subject. The described capsule is constructed of individual layers separated by a plurality of air spaces, and acoustically absorptive material. However the acoustic noise attenuation system is constructed in means designed especially to isolate noise and vibration, in a multiuse apparatus. Moreover the preferred embodiment design of the system includes two openings at least for the patient to be accessed, and it is not known how this arrangement would function in case of an immediate need.

There is a need for a patient transport incubator in which the envelope separating the patient from the environment is a dedicated thermo-regulation noise reducing enclosure, and as such includes a thickened envelope made of MRI safe thermo-isolating noise reducing foam. Furthermore there is a need for a one time use, disposable envelope in order to maintain a sterile patient environment. The patient transport incubator of the present invention will allow easy access in a single step to the patient within. In addition the envelope comprising MRI safe foam will limit patient movements resulting in better quality imaging, and less need to repeat process.

SUMMARY OF THE INVENTION

The present invention provides a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam.

It is another object of the current invention to disclose the PTI as described above, comprising an envelope, wherein the envelope is configured for at least one open position for accommodating the patient, and at least one closed position configured to at least partially confine the patient within the inner volume.

It is another object of the current invention to disclose the PTI as described above, wherein at least one of the following holds true: (a) the envelope is configured to separate the patient tissues from coming into contact with the MRI bore; (b) the envelope shape is selected from a group consisting of: patient ergonomic, none ergonomic, patient movement restrictive shape, and any combination thereof; and, (c) the envelope is defined by means of size and shape to enable the placement of the patient's body such that the body does not form electrically conducting loops.

It is another object of the current invention to disclose the PTI as described above, comprising at least one sensor configured to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

It is another object of the current invention to disclose the PTI as described above, comprising an envelope, wherein the envelope is configured to house at least one reversibly connectable module selected from a group consisting of: a temperature regulating vent module, a venting module, a user interface module, a control unit module, at least one life support system module, a monitoring module, a sensor module, and any combination thereof.

It is another object of the current invention to disclose the PTI as described above, wherein the PTI is configured to change at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

It is another object of the current invention to disclose the PTI as described above, wherein the envelope further comprises at least one selected from a group consisting of: a sound absorptive material, a resonator, a sound shield, a bass trap, a sound baffle, a diffuser, an insulation padding, a sound reflector, a sound muffler, and any combination thereof, configured to change the sound signature reaching the patient.

It is another object of the current invention to disclose the PTI as described above, wherein at least a portion of the envelope comprises n layers; further wherein each of the n layers comprising an inner side towards the inner volume, and an opposite outer side facing towards the environment; further wherein each of the n layers comprising a predefined Noise Reduction Coefficient (NRC) value, Sound Transmission Class (STC) value, or both; further wherein the NRC value, STC value, or both, can be equal or different for the each of one of n layers.

It is another object of the current invention to disclose the PTI as described above, wherein each of the layers comprising at least one sound level $S_1$ [dB] measured on the layer outer side, and at least one first sound level $S_n$ [dB], measured on the layer inner side, having a $dS_1$-...$dS_n$, wherein dS of the PTI equals $S_1-S_n$, and $S_1-S_n<S_1$.

It is another object of the current invention to disclose the PTI as described above, characterized by an elongated shape, having a main longitudinal axis with a proximal end and an opposite distal end; the PTI further comprising in at least one of the ends, a temperature regulating vent (TRV); the TRV is adapted to stream air from the end towards the opposite end substantially along the axis; and is configured, by means of size and shape, to accommodate the patient in parallel to the axis; further wherein the TRV is a module selected from a group consisting of at least one first venting module, at least one first heating/cooling module, at least one filter located adjacently to either the first venting module or the first heating/cooling module, at least one humidifying module and any combination thereof.

The present invention provides a method of magnetic resonance imaging of patients comprising steps of: (a) obtaining a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam; (b) placing the patient into the enveloped inner volume; and, (c) introducing the PTI into the MRI open bore and imaging.

The present invention provides a standard of care protocol for MRI of patients, comprising steps of: (a) obtaining a PTI suitable for magnetic resonance imaging device (MRD) with an open bore, the incubator comprising an inner volume having a first set of dimensions, the inner volume is adapted by means of shape and size to accommodate the patient, the inner volume further is covered by an envelope having a second set of dimensions, adapted by shape and size to be temporarily introduced within the open bore; when at least a portion of the envelope comprises MRI-safe thermo-isolating and noise reducing foam, confining the compartment from its environment; (b) placing the patient into enveloped inner volume; and, (c) introducing the incubator into MRI open bore and imaging; wherein at least one of the following is held true: (a) the sound pressure measured inside the PTI does not exceed a maximum level of 60 dB; and the sound level in the inner volume of the PTI compartment would be at least 10 dB lower than the sound level outside this compartment; (b) the sound pressure measured inside the PTI does not exceed a maximum level of 45 dB; and the sound level in the inner volume of the PTI compartment would be at least 10 dB lower than the sound level outside this compartment; (c) the average value of salivary cortisol level index from noise derived stress of patient when utilizing the PTI during MRI is n times lower than the average the value during MRI; n is equal or greater than 1.05; (d) the average number of movements per minute of patient when utilizing the PTI during MRI is m times lower than the average number of movements per minute of the patient; m is equal or greater than 1.05; the average number of MRI repetition number per patient is p times lower when utilizing the PTI than the average number of MRI repetitions during MRI of patients; p is equal or greater than 1.05; (e) the average value of salivary cortisol level index from open space related stress of patient when utilizing the PTI during MRI is q times lower than the average the value during MRI; q is equal or greater than 1.05; (f) the temperature of the inner volume of the PTI is at the most 2° C. different than the control temperature of 36° C.; (g) the $O_2$ concentration within the PTI does not fall below 30 vol. %, and does not exceed 40 vol. %; (h) the $CO_2$ concentration within the PTI does not exceed 4%; (i) the air velocity over the mattress within the PTI does not exceed 0.35 m/s; (j) the average humidity levels of the inner volume of the PTI are maintained for the duration of MRI as medically predetermined by medical personal at levels of up to 85%; (k) the PTI will continue to be used safely in occurrence of a leakage of up to 200 ml deposited in the compartment of the PTI; (l) the PTI will remain stable when tilted 10° in normal use and when tilted 20° during transportation; (m) the PTI will not tip over when the force is 100 N or less; (n) the average number of patients MRI related fall incidents when utilizing the PTI is r times lower than the average of patients MRI related fall incidents; r is equal or greater than 1.05; (o) the average number of patient infections acquired that are MRI associated, when utilizing the PTI, is s times lower than the average number of infections acquired by patients that are MRI associated; s is equal or greater than 1.05; (p) the average number of MRI associated patient's health complications when utilizing the PTI is t times lower than the average number of the patient's MRI associated health complications, t is equal or greater than 1.05; (q) the radiated electromagnetic fields in the inner volume of the PTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (r) the average number of excessive heating incidents and burn incidents in association with the MRI is u times lower when utilizing the PTI; u is equal or greater than 1.05.

The present invention provides a patient transport incubator (PTI) suitable for MRI device having an open bore; the PTI comprises an inner volume having a first set of dimensions, adapted by means of shape and size to accommodate at least a portion of an MRI-compatible neonate's cradle, the inner volume is further covered by an envelope having a second set of dimensions, adapted by means of shape and size to be temporarily introduced within the open bore; wherein at least a portion of the envelope comprises MRI safe thermo-isolating and noise reducing foam.

It is another object of the current invention to disclose the PTI as described above, comprising an envelope, wherein the envelope is configured for at least one open position for accommodating the MRI-compatible neonate's cradle, and at least one closed position configured to at least partially confine the MRI-compatible neonate's cradle within the inner volume.

It is another object of the current invention to disclose the PTI as described above, wherein at least one of the following holds true: (a) the envelope is configured to separate patient tissues from coming into contact with the MRI bore; (b) the envelope shape facing the inner volume is selected from a group consisting of: patient ergonomic, none ergonomic, patient movement restrictive shape, and any combination thereof; and, (c) the envelope is defined by means of size and shape to enable the placement of the patient's body such that the body does not form electrically conducting loops.

It is another object of the current invention to disclose the PTI as described above, comprising at least one sensor configured to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

It is another object of the current invention to disclose the PTI as described above, comprising an envelope, wherein the envelope is configured to house at least one reversibly connectable module selected from a group consisting of: a temperature regulating vent module, a venting module, a user interface module, a control unit module, at least one life support system module, a monitoring module, a sensor module, and any combination thereof.

It is another object of the current invention to disclose the PTI as described above, wherein the PTI is configured to change at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

It is another object of the current invention to disclose the PTI as described above, wherein the envelope further comprises at least one selected from a group consisting of: a sound absorptive material, a resonator, a sound shield, a bass trap, a sound baffle, a diffuser, an insulation padding, a sound reflector, a sound muffler, and any combination thereof, configured to change the sound signature reaching the patient.

It is another object of the current invention to disclose the PTI as described above, wherein at least a portion of the envelope comprises n layers; further wherein each of the n layers comprising an inner side towards the inner volume, and an opposite outer side facing towards the environment; further wherein each of the n layers comprising a predefined Noise Reduction Coefficient (NRC) value, Sound Transmission Class (STC) value, or both; further wherein the NRC value, STC value, or both, can be equal or different for the each of one of n layers.

It is another object of the current invention to disclose the PTI as described above, wherein: each of the layers comprising at least one sound level $S_1$ [dB] measured on the layer outer side, and at least one first sound level $S_n$ [dB], measured on the layer inner side, having a $dS_1$- . . . $dS_n$, wherein dS of the PTI equals $S_1$-Sn, and $S_1$-Sn<$S_1$.

The present invention provides a method of magnetic resonance imaging of patients comprising steps of: (a) obtaining a patient transport incubator (PTI) suitable for MRI device having an open bore; the PTI comprises an inner volume having a first set of dimensions, adapted by means of shape and size to accommodate at least a portion of an MRI-compatible neonate's cradle, the inner volume is further covered by an envelope having a second set of dimensions, adapted by means of shape and size to be temporarily introduced within the open bore; wherein at least a portion of the envelope comprises MRI safe thermo-isolating and noise reducing foam; (b) placing neonate into the neonate's cradle; (c) placing the neonate's cradle into the enveloped inner volume; and, (d) introducing the incubator into the MRI open bore and imaging.

BRIEF DESCRIPTION OF THE DRAWINGS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

FIG. 1A is a schematic illustration of a PTI (100) in a cylindered embodiment;

FIG. 1B is a schematic illustration of a cross section view of a PTI (100) in a cylindered embodiment, along the line of A in FIG. 1;

FIG. 2A is a schematic illustration of an infant transport incubator (100) in a rectangular embodiment;

FIG. 2B is a schematic illustration of a cross section view of an infant transport incubator (100) in a rectangular embodiment, along the line of A in FIG. 2;

DETAILED DESCRIPTION OF THE PREFERRED EMBODIMENTS

Figure 2C:
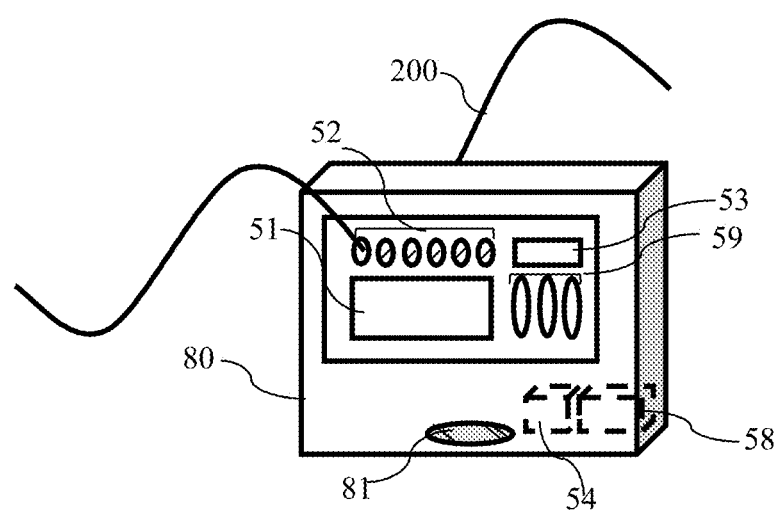
FIG. 2C is a schematic illustration of an embodiment of a detachable user interface (80)

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam.

Further the present invention provides a patient transport incubator (PTI) suitable for magnetic resonance imaging device (MRD) is provided. The MRD, having an open bore, the incubator comprising an inner volume, having a first set of dimensions, the inner volume is adapted by means of shape and size to accommodate at least a portion of MRI-compatible neonate's cradle, as depicted in patent 226488 IL, dated 21 May 2013 and is incorporated in its entirety; the inner volume further is covered by an envelope having a second set of dimensions, adapted by shape and size to be temporarily introduced within the open bore; wherein at least a portion of the envelope comprises thermo-isolating MRI safe, non-interfering noise reducing foam, separating the inner volume from its environment.

A PTI comprising at least a portion of thermo-isolating MRI-safe foam will increase the safety of MRI, as the body temperature of the patient will be maintained. The noise reducing qualities of the PTI will protect the patient's hearing and reduce noise related stress. The PTI will reduce stress related health complications and unnecessary repetitions of MRI.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR), any Laser magnetic resonance device, any Quantum Rotational field magnetic resonance device (cyclotron), and any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device.

The term "MRI-safe" interchangeably refers herein to any material that, when used in the MR environment, will present no additional risk to the patient and not significantly affect the quality of the diagnostic information. The material is completely non-magnetic, non-electrically conductive, and non-RF reactive, eliminating all of the primary potential threats during an MRI procedure.

The term "open bore" interchangeably refers herein after to MRD's open bore and to C-shape MRD's open yolk.

The term "patient" interchangeably refers herein after to a term selected from a group of: neonate, baby, infant, toddler, child, adolescent, adult, elderly, etc.; further this term refers to person or animal.

The term "handler" interchangeably refers herein after to a term selected from a group of: medical personal, maintenance personal, chaperon and technician.

The term "foam" interchangeably refers hereinafter to materials such as Styrofoam® commercially available from The Dow Chemical Company, polystyrene foam, high-impact polystyrene, polybutadiene, polyurethane foam, polyvinyl chloride foam, polyimide foam, silicone foam, polymethacrylimide foam, polypropylene foam, polyethylene foam, syntactic foam, rubber, polybutadiene rubber, carbon, cellulose, starch, graphite, acrylonitrile, maleic anhydride, divinylbenzene, aerogel, silica aerogel, ceramics, polyisocyanurate, cementitious foam, glass, silica, etc. Further this foam is open cell, closed cell foam, and can contain micro-balloons of an additional material such as glass, carbon, epoxy, etc., or alternatively, the foam can be composite foam, these are acoustical foams that are made by layering different facings or foams together to create enhanced performance for specific application types. Additionally or alternatively, the foam can be porous, non-porous, at least partially flexible, rigid, liquid absorbent, lightweight, The term "fire retardant materials" interchangeably refers hereinafter to materials such as tetrabromobisphenol-a, decabromdiphenyl ether, hexabromcyclododecane, chloroparaffins, dedecachloro-pentacyclooctadecadiene, diphenyl phosphate, triaryl phosphates, metal phosphinates, 9,10-dihydro-9-oxa-10-phosphaphenanthrene-10-oxide, trischloropropyl phosphate, ammonium polyphosphate, red phosphorous, melamine, melamine cyanurate, melamine polyphosphate, melamine polyzinc, melamine polyaluminum, phosphates, melamine-based HALS (Hindered Amine Light Stabilizer), intumescent flame retardant systems, metal hydroxides, zinc compounds antimony trioxide, expandable graphite, organo-layered silicates, natural oil polyols etc.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride etc.

The term "compartment" interchangeably refers herein to the inner volume of the infant incubator defined by means of shape and size.

The term "mattress" interchangeably refers herein to the part of the inner envelope on which the patient is placed.

The term "CPU-central processing unit" interchangeably refers hereinafter to the hardware within a computer that carries out the instructions of a computer program by performing the basic arithmetical, logical, and input/output operations of the system.

The term "sensing equipment" interchangeably refers hereinafter to any device that receives a signal or stimulus (heat, pressure, light, motion, sound, humidity etc.) and responds to it in a distinctive manner.

The term "visual indicators" interchangeably refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "audible indicators" interchangeably refers hereinafter to a representation of sound, typically as an electrical voltage. Audible indicators have frequencies in the audio frequency range of roughly 20 to 20,000 Hz (the limits of human hearing). Audible indicators may be synthesized directly, or may originate at a transducer such as a microphone, musical instrument pickup, phonograph cartridge, or tape head.

The term "sensible indicators" interchangeably refers hereinafter to a physical movement of at least a portion of the user interface, which is noticeable to the user (shaking, vibrating, quivering, etc.).

The term "quick release mechanism" interchangeably refers hereinafter to a mechanism such as quick release: fastener, draw latch, latch, lock, belt, bolt, grip, bar, bond, clamp, clasp, connection, fixture, link, hook, hasp, buckle, harness, clip, snap, pin, peg, grapnel, etc., that facilitates fast disconnecting of incubator envelope parts that will enable the quick/immediate release of the patient.

The term "ergonomic" interchangeably refers hereinafter to the design of the incubator configured to minimize discomfort of the user, handler or both. The incubator is designed in a manner that fits the patient's body and its cognitive abilities. More specifically this term relates to the placement within the inner volume of the incubator to fit by means of size, shape, surface properties, sound transmission, light transmission, etc., to be appropriate for maximizing the well-being of the patient. This term further relates to the human interface of the incubator designed for the handler, parts such as the user interface, open and close mechanisms, overall size and shape, connections to other equipment, etc., are all designed in a manner that takes into consideration human factors.

The term "lock mechanism" interchangeably refers hereinafter to a mechanism that connects the incubator to other equipment such as: patient tray, gurney, patient bed, trolley, push chair, wheelchair, perambulator, table, bar, bench, board, counter, desk, stand, console, trolley, etc.

The term "medical equipment" interchangeably refers hereinafter to all devices, tubes, connectors, wires, liquid carriers, needles, sensors, etc., that are used by medical staff in association with the patient. This medical equipment is used for various purposes such as life support, MRI contras solution injection, monitoring of cardio and breathing rates, etc.

The term "electrical equipment" interchangeably refers hereinafter to all devices powered by electricity from any source such as alternating current (AC), direct current (DC) or both. Further this current is supplied internally, externally or both.

The term "user interface" interchangeably refers hereinafter to at least one defined area in which the user interacts with the incubator. This area harbors: passage for medical equipment, display, CPU, alarm system, monitoring system, power supply, open mechanism, close mechanism, indicators, etc. The user interface is designed for the handler, user or both.

The term "module" interchangeably refers hereinafter to a structurally independent part, able to be connected and detached from incubator. This module is connected itself or by another element in its contour, embedded, integrated, placed, interconnected, housed, contained, etc. to the incubator.

The term "user interface module" interchangeably refers hereinafter to a module that organizes at least one of the elements in which the handler or user interact with.

The term "venting module" interchangeably refers hereinafter to a module that circulates air and distributes it either evenly or in a defined direction. More specifically the term relates to a fan, a jet, a blower, a compressor, a pump, etc.

The term "heating/cooling module" interchangeably refers hereinafter to a module that controls the temperature either by heating or by cooling or by doing both. More specifically the term relates to an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module, etc.

The term "predetermined values" interchangeably refers hereinafter to medical values such as respiration, cardiac function, blood oxygenation, brain activity; environmental values such as temperature, humidity, $O_2$, $CO_2$, sound pressure levels, vibrations, drift, electricity, radio frequency; system values such data transfer, opened or closed state of incubator envelope, structural integrity of incubator, structural integrity of interconnected parts, general function of incubator.

The term "stress index of salivary cortisol levels" interchangeably refers hereinafter to stress evaluated by the measurement of cortisol levels in the saliva.

The term "medical facility" interchangeably refers hereinafter to any facility providing medical services such as medical care, medical testing, laboratory, etc.

The term "connection", in reference to the PTI parts and modules, interchangeably refers hereinafter to any contact, relation, association, integration, interconnection, joining etc., of the PTI parts and modules to one another and to third party.

The term "human hearing" interchangeably refers herein to any sound received by the human ear, with the typical frequency range for normal hearing being between 20-Hz to 20,000-Hz. The logarithmic decibel scale, dB, is used when referring to sound power.

The term "decibels" or "dB", interchangeably refers herein to the unit used to express the ratio between two values of such as an amplitude. If sound power ratios are x and amplitude ratios √x then dB equivalents 10 $\log_{10}$X. As depicted in Wikipedia, when referring to measurements of field amplitude, it is usual to consider the ratio of the squares of $A_1$ (measured amplitude) and $A_0$ (reference amplitude). Thus, the following definition is used:

$$L_{dB} = 10\log_{10}\left(\frac{A_1^2}{A_0^2}\right) = 20\log_{10}\left(\frac{A_1}{A_0}\right).$$

A change in power ratio by a factor of 10 is a change of 10 dB. The decibel is commonly used in acoustics as a unit of sound pressure, for a reference pressure of 20 micropascals in air and 1 micropascal in water. The reference pressure in air is set at the typical threshold of perception of an average human and there are common comparisons used to illustrate different levels of sound pressure. Sound pressure is a field quantity, therefore the field version of the unit definition is used:

$$L_p = 20\log_{10}\left(\frac{p_{rms}}{p_{ref}}\right) \text{dB}$$

where $p_{ref}$ is equal to the standard reference sound pressure level of 20 micropascals in air or 1 micropascal in water.

On the decibel scale, the smallest audible sound (near total silence) is 0 dB. Here are some common sounds and their decibel ratings as known in the art: Near total silence—0 dB, A whisper—about 15 dB, Normal conversation—about 40-60 dB, A lawnmower—90 dB about, A car horn—about 110 dB, A rock concert or a jet engine—about 110-150 dB, A gunshot or firecracker—140 dB. It is known in the art that any sound above 85 dB can cause hearing loss, and the loss is related both to the power of the sound as well as the length of exposure. Eight hours of 90-dB sound can cause damage to your ears; any exposure to 140-dB sound causes immediate damage (and causes actual pain).

According to one embodiment of the invention, the PTI is configured to maintain the sound levels at 45 dB or lower within the inner volume.

The term "sound" interchangeably refers herein to any audible acoustic waves, as depicted in Wikipedia, sound is a vibration that propagates as a typically audible mechanical wave of pressure and displacement, through a medium such as air or water, when intercepted by any human, animal or any mechanical device or receiver. It is in the scope of the present invention that sound can be characterized by at least one of the following parameters: sound levels (can be measured in as sound pressure or in decibels [dB], overtone composition, reverberations, sound frequency [Hz], sound wavelength [feet or meters], tone, sound wave amplitude, sound wave velocity [meters per sec. or feet per sec], sound wave direction, timbre, sound wave phase, sound wave shape, sound envelope, and, sound wave energy [joules]. Any of the aforementioned characteristics can be used to define a sound signature. It is in the scope of the present invention that noise reduction is any desired change in at least one characteristic of the sound signature of the environment.

The term "wave shape" is the actual shape of the wave. Some different types of waves are: sine waves, trapezoid waves, square waves, triangle waves, saw tooth waves, curved waves, linear waves and any combination thereof. It is the unique combination of the fundamental wave and the harmonics that gives a sound its timbre (the tone color, or the quality, of a sound). Timbre is also defined by the sound envelope. The Envelope is kind of a combination of amplitude and wavelength—it describes the individual parts of a sound, broken down into ADSR (Attack, Decay, Sustain, Release). Attack—How a sound is started after the sound source begins to vibrate; Decay—the initial dying off after the attack; Sustain—when the sound remains relatively constant after the initial decay; Release—the time period and manner in which a sound fades to nothing, (http://www.audioduct.com/Lessons). According to another embodiment of the invention the sound wave of the sound signature can be harmonic or non-harmonic. Additionally or alternatively the waves are of the same or different harmonics levels.

The term "sound wave phase" refers herein to the time relationship between two waves. In-Phase—the waves are working together; (compression and rarefaction occur in both waves at the same time.) This increases the amplitude. If two waves are totally in-phase, then amplitude is increased by three dB. Out-of-Phase—the waves are working against each other (compression is occurring in one wave while rarefaction is occurring in in the other. If the waves are completely out of phase (180°), there will be extreme cancellation.

It is further in the scope of the present invention that the envelope foam provides noise reducing qualities by allowing a different sound signature to enter the inner volume of the incubator than the sound generated by any noise generator in the environment. Therefor the envelope can completely attenuate the sound generated by the noise generator such that it is not auditable within the limits of the human hearing within said inner volume, additionally or alternatively, the sound can be attenuated partially, completely, or attenuated in at least one of the sound characteristics, therefore creating a new sound signature.

The term "noise" interchangeably refers herein to any unwanted sound defined in terms of frequency spectrum (in Hz), intensity (in dB), and time duration. The sound is also defined by its sound signature. Noise can be steady-state, intermittent, impulsive, or explosive. Transient hearing loss may occur following exposure to loud noise, resulting in a temporary threshold shift (i.e., a shift in the audible threshold). This term further includes harmonious and/or non-harmonious sounds, intended and/or unintended such as: a melody, tapping, banging, chirping, squeaking, blast, buzz, cacophony, clamor, commotion, crash, echo, cry, explosion, roar, babel, bang, bellow, blare, boom, caterwauling, clang, clatter, detonation, din, discord, disquiet, disquietude, drumming, eruption, jangle, lamentation, outcry, pandemonium, peal, racket, knocking, shot, shouting, squawk, stridency, thud, uproar, yell, music, or any combination thereof including a single or plurality of each. Noise tends to be enhanced by decreases in section thickness, field of view, repetition time, and echo time. Furthermore, noise characteristics have a spatial dependence. For example, noise levels can vary by as much as 10 dB as a function of patient position within a defined space such as the bore of a magnetic resonance system or within an incubator. The presence and size of the patient may also affect the level of acoustic noise. Airborne sound travels through the air and can transmit through a material, assembly or partition. Sound can also pass under doorways, through ventilation, over, under, around, and through obstructions. When sound reaches a room where it is unwanted, it becomes noise. Further, noise can be prolonged and multiplied by reverberations and reflections.

Additionally or alternatively the noise can originate from such as: a medical device operation, a scanning device, an incubator in communication with a motor, noise derived of an attached medical device, life support equipment, a venting mechanism, a thermo regulating system, an air filtering system, a humidifier, rapid alterations of currents within magnetic resonance coils, an external alarm, external speech sounds, closing or opening of the incubator, handling of equipment in the incubator vicinity, and etc.

It is in the scope of the present invention that the foam is provided as a passive sound absorptive material, having at least a portion of sound energy dissipated within the medium itself as sound travels through it. Absorbing materials can be such as porous materials commonly formed of matted or spun fibers. Common porous absorbers allow air to flow into a cellular structure where sound energy is converted to heat. These may include a thick layer of cloth or carpet, spray-applied cellulose, aerated plaster, fibrous mineral wool and glass fiber, open-cell foam, and felted or cast porous ceiling tile.

It is further in the scope of the present invention that additional layers of the same foam or another acoustic insulation material is used to provide noise attenuation, incorporated in connection with the incubator; from within, on top, bottom, side, front, back, at least partly enveloping the incubator, along at least a portion of the incubator inner volume and etc.

Resonators can also absorb sound, this is created by holes or slots connected to an enclosed volume of trapped air. The term "resonators" interchangeably refers herein to a structure configured to typically act to absorb sound in a narrow frequency range. Resonators include some perforated materials and materials that have openings (holes and slots). Such as a Helmholtz resonator, which has the shape of a bottle. The resonant frequency is governed by the size of the opening, the length of the neck and the volume of air trapped in the chamber.

According to another embodiment of the invention, a PTI as described above is disclosed further comprising foam embedded with holes or slots configured to provide sound absorbing resonators. According to another embodiment of the invention, the envelope comprises at least one concave shape or slot configured to house at least one selected from a group consisting of: insulation material, sound diffuser, sound resonator, sound shield, sound baffle, sound reflector, sound absorbing material, sound absorber, and any combination thereof.

Other absorbers are panel absorbers. Typically, panel absorbers are non-rigid, non-porous materials which are placed over an airspace that vibrates in a flexural mode in response to sound pressure exerted by adjacent air molecules for example thin wood paneling over framing, lightweight impervious ceilings and floors, glazing and other large surfaces capable of resonating in response to sound. An absorber is configured to reduce the acoustic noise by absorbing the sound energy, when sound waves collide with the absorber (as opposed to reflecting the energy); where at least part of the absorbed energy is transformed into heat or movement energy. Additionally or alternatively, absorptive surface treatments to the envelope, foam or both, can help to eliminate both reverberation and reflection problems.

It is further in the scope of the invention wherein the foam is provided as a mass barrier configured to at least partially prevent the transmission of noise to the incubator inner environment. It is further in the scope of the present invention that the foam is provided as a porous sound absorbing material.

According to another embodiment of the invention a PTI as described above is disclosed further comprising vibration damping and/or vibration isolation means. The can be such as any flexible elements such as rubber, spring, cork or physical brake.

The term "Acoustic insulation material" or "sound insulation padding" interchangeably refers herein to any material with the ability to absorb sound, act as a barrier of sound, or both. This can refer in a non-limiting manner to materials such as: cork, wool, cotton, Eel grass, fiber glass, glass wool, wood, paper, Cobalt Quilt, sugarcane, hydrated Calcium sulphate, POP, Coir, plastic, PVC, perforated metal, Mineral fiber board, or Micore, Thermocole, Polyurethane, Jute, Mylar film, melamine, rubber, rock wool, cellulose, polystyrene, polyethylene, polyester, any of these materials when recycled, and etc. Further the acoustic material can be in one or more forms such as a sheet, fabric, tile, blanket, foam, rug, carpet, drape, curtain, panel, board, any casted shape, rod, block, beads, straw like, gravel like particles, Fabric can be wrapped around substrates to create what is referred to as a "pre-fabricated panel", and any combination thereof. Additionally or alternatively, the insulation material can be at least partially constructed from Composite foams. Composite foams can meet more than one acoustical requirements at the same time such as providing both sound blocking and sound absorbing capabilities. These can be open or closed cell foams. Additionally or alternatively all the aforementioned materials can be at least partly porous. Additionally or alternatively, all the aforementioned materials can be combined with fire resistant materials. It is in the scope of the present invention that the MRI safe thermo regulating, noise reducing foam is an acoustical insulating material, and/or is further embedded/covered with acoustical insulating material.

The term "Bass Traps" interchangeably refers herein to acoustic energy absorbers which are designed to damp low frequency sound energy with the goal of attaining a flatter low frequency (LF) room response by reducing LF resonances in rooms. Similar to other acoustically absorptive devices, they function by turning sound energy into heat through friction. There are generally two types of bass traps: resonating absorbers and porous absorbers. By their nature resonating absorbers tend toward narrow band action [absorb only a narrow range of sound frequencies] and porous absorbers tend toward broadband action [absorbing sound all the way across the audible band—low, mid, and high frequencies], though both types can be altered to be either more narrow, or more broad in their absorptive action. Examples of resonating type bass traps include Helmholtz resonators, and devices based on diaphragmic elements or membranes which are free to vibrate in sympathy with the room's air when sound occurs.

According to another embodiment of the invention, a PTI as described above is disclosed, wherein said envelope comprises a selected from a group consisting of at least one bass trap, at least one absorbing resonator, at least one porous resonator, at least one diffuser and any combination thereof.

It is in the scope of the invention wherein the term "diffusion" refers to the efficacy by which sound energy is spread evenly in a given environment. A perfectly diffusive sound space is, as defined in Wikipedia, one that has certain key acoustic properties which are the same anywhere in the space. A non-diffuse sound space would have considerably different reverberation time as the listener moved around the room. Spaces which are highly non-diffuse are ones where the acoustic absorption is unevenly distributed around the space, or where two different acoustic volumes are coupled. The diffusiveness of a sound field can be measured by taking reverberation time measurements at a large number of points in the room, then taking the standard deviation on these decay times. Small sound spaces generally have very poor diffusion characteristics at low frequencies due to room modes.

Still in the scope of the invention, "diffusors", and "diffusers" are interchangeably used herein to define means to treat sound aberrations within a medical device, such as echoes. As depicted in Wikidepia, diffusers are an excellent alternative or complement to sound absorption because they do not remove sound energy, but can be used to effectively reduce distinct echoes and reflections while still leaving a live sounding space. Compared to a reflective surface, which will cause most of the energy to be reflected off at an angle equal to the angle of incidence, a diffusor will cause the sound energy to be radiated in many directions, hence leading to a more diffusive acoustic space. It is also important that a diffusor spreads reflections in time as well as spatially. Diffusors can aid sound diffusion, but this is not why they are used in many cases; they are more often used to remove coloration and echoes. The term 'diffusers' also relates to MLS Diffusors, 1000 Hz Quadratic-Residue Diffusor, Primitive-Root Diffusors, Optimized Diffusors, Two Dimensional ("Hemispherical") Diffusors etc.

The term "sound baffle" interchangeably refers herein to a construction or device which reduces the strength (level) of airborne sound, as measured in dB (decibels). Sound baffles are a fundamental tool of noise mitigation, for the practice of minimizing noise or reverberation. An important type of sound baffle is a noise barrier/sound shield. Sound baffles are also applied to walls and ceilings in building interiors to absorb sound energy and thus lessen reverberation. These include, as non-limiting examples, wave baffles, fabric coated baffles, curtain baffles, panel baffles and etc.

It is further within the scope of the invention an incubator, comprising an envelope fitted for housing a neonate, comprising at least one air flow opening, the opening comprising at least one selected from a group consisting of: a resonator, a sound baffle, a diffuser, a bass trap, a sound muffler, a sound shield, configured to attenuate sound. Additionally or alternatively, the envelope comprises volume having height represented by h, and is measured preferably in millimeters. The value of h can be constant or variable throughout the medical device. In at least a portion of this volume resonators and/or attenuators can be implemented. Further this volume can be filled with sound absorptive material situated around and/or within the perforations.

The term "sound shield" refers herein after to any sound barriers or sound reflection panel, sound absorbing panel, screens, baffle, or any combination thereof, single or a plurality of, configured to lowering the sound reaching the patient.

The term "reverberation" interchangeably refers herein to a prolongation of the sound in the room caused by continued multiple reflections is called reverberation. This can happen in an at least partially enclosed space during the time it takes a sound to become inaudible and stop emitting energy. When room surfaces are highly reflective, sound continues to reflect or reverberate. The effect of this condition is described as a live space with a long reverberation time. A high reverberation time will cause a build-up of the noise level in a space.

The term "reflection" interchangeably refers herein to a phenomenon that sound reflects back from at least one surface or object before reaching the receiver. These reflections can have unwanted or even disastrous consequences. Reflective corners or peaked ceilings can create a "megaphone" effect potentially causing annoying reflections and loud spaces. Reflective parallel surfaces lend themselves to a unique acoustical problem called standing waves, creating a "fluttering" of sound between the two surfaces. The standing waves can produce natural resonances that can be heard as a pleasant sensation or an annoying one. Reflections can be attributed to the shape of the space as well as the material on the surfaces. Domes and concave surfaces cause reflections to be focused rather than dispersed which can cause annoying sound reflections.

The term "NRC" or "Noise Reduction Coefficient" interchangeably refers herein to a characteristic of a material/product presenting the average absorption across four octave band center frequencies. (250 Hz, 500 Hz, 1000 Hz, 2000 Hz.). It can be roughly estimate that a product with an NRC 0.75 will absorb about 75% of the sound energy that hits it. The highest level is NRC 1.0. Substantially this is the average of the mid frequency absorption rate, rounded to the near 5%, and does not include the high and low frequencies.

The term "STC" or "Sound Transmission Class" interchangeably refers herein to a number rating of the transmission loss properties of a material and/or product. It is a single-number rating of a material's or an assembly's ability to resist airborne sound transfer at the frequencies 125-4000 Hz. Substantially, this refers to a material's barrier ability qualities. In general, a material/product with higher STC rating blocks more noise from transmitting through a partition. STC is highly dependent on the construction of the partition. A partition's STC can be increased by: adding mass, increasing or adding air space, adding absorptive material within the partition, and likewise. A partition is given an STC rating by measuring its Transmission Loss over a range of 16 different frequencies between 125-4000 Hz. The STC rating does not assess the low frequency sound transfer. Doors, windows, walls, floors, etc. are tested to determine how much noise passes through.

The term "about" interchangeably refers herein to a divergence of up to plus or minus 20% around a given value.

According to one embodiment of the present invention, a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam.

According to another embodiment of the invention, a PTI as defined above is disclosed, comprising an enveloped inner volume, wherein at least a portion of the envelope is integrated with fire retardant materials.

According to another embodiment of the invention, a PTI as defined above is disclosed, wherein the envelope comprises at least one opening.

According to another embodiment of the invention, a PTI as defined above is disclosed, comprising at least two connected parts, wherein the parts are connected by means such as hinge, joint, hook, link, bridge, clamp, bond, bracket, clasp, lock, snap, brace, grip, juncture, interweave, threading, etc.

According to another embodiment of the invention, a PTI as defined above is disclosed, comprising an envelope with at least one open position and one closed position.

According to another embodiment of the invention, a PTI as defined above is disclosed, wherein the open position is achieved by moving at least a part of the envelope relative to another part of the envelope that remain in a fixed position. This movement enables the envelope parts be to completely separate or remain connected in at least a portion of the envelope.

According to another embodiment of the invention, a PTI as defined above is disclosed, wherein the connection between the envelope parts is defined by means of location, material and shape to isolate the inner volume of the envelope from the outside conditions selected from a group consisting of: temperature, humidity, sound, vibration, $O_2$ concentration, $CO_2$ concentration and any combination thereof.

According to another embodiment of the invention, a PTI as defined above is disclosed, wherein the envelope is formed in at least one of a plurality of shapes such as substantially cylindered, spherical, rectangular, polygonal, polymorphic, symmetrical, none symmetrical, concave, ergonomic, etc.

According to another embodiment of the invention, a PTI as defined above is disclosed, wherein at least one of the following holds true: (a) the opening further comprises at least one sound attenuating means configured to muffle the sound passing through the opening; (b) the opening is adapted by means of size and shape for the passage of equipment selected from a group consisting of: tubing, life supporting, monitoring, sensing, temperature maintaining, ventilating and any combination thereof and, (c) the opening is adapted by means of size and shape to allow passage of a handler's hand.

According to another embodiment of the invention, a PTI as defined above is disclosed, further comprising acoustical insulation material.

According to another embodiment of the invention, a PTI as defined above is disclosed, comprising an envelope, wherein the envelope is configured for at least one open position for accommodating the patient, and at least one closed position configured to at least partially confine the patient within the inner volume.

According to another embodiment of the invention, a PTI as defined above is disclosed, wherein the envelope is defined by means of size and shape to fit a specific pre-defined patient body position as defined by medical needs.

According to another embodiment of the invention, a PTI as defined above is disclosed, wherein a mechanism attaches the patient transport incubator to the MRI bore; The attaching mechanism operates by: belting, screwing, hammering, fitting, sliding, tracking, latching, locking, joining, affixing, embedding, interweaving, clamping, coupling, locking, implanting, attaching, linking, adhering, stamping, covering, layering, connecting, interconnecting, hooking, inserting, engulfing etc. Further this attachment is a fast release mechanism, enabling fast extraction of the patient transport incubator from where it was attached. Further this attachment mechanism is attached to the incubator on one side, and to the MRD itself or other objects in the MRD open bore or such as patient support table, trolley, board, gurney, bed, etc., on the other side. This mechanism prevents tipping over and fall of the incubator.

According to another embodiment of the invention, a PTI as defined above is disclosed, wherein the envelope comprises a quick release mechanism enabling rapid access to a patient within the inner volume.

According to another embodiment of the invention, a PTI as defined above is disclosed, comprising at least a portion of at least partially transparent material, wherein the transparent material enables at least a part of the patient to be observed visually.

According to another embodiment of the invention, a PTI as defined above is disclosed, wherein at least one of the following holds true: (a) the envelope separates patient tissues from coming into contact with the MRD bore; (b) the envelope shape is selected from a group consisting of: patient ergonomic, none ergonomic, patient movement restrictive shape, and any combination thereof; and, (c) the envelope is defined by means of size and shape to enable the placement of the patient's body such that the body does not form electrically conducting loops.

According to another embodiment of the invention, a PTI as defined above is disclosed, comprising at least one sensor configured to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

According to another embodiment of the invention, a PTI as defined above is disclosed, comprising sensing equipment wherein the equipment is connected embedded, integrated, layered, interconnected, fitted, placed, interweaved, adhered, implanted, nested, etc. to at least a portion of the PTI.

According to another embodiment of the invention, a PTI as defined above is disclosed, comprising sensing equipment, further comprising at least one indicator, wherein the equipment responds to at least one signal by transmitting data to at least one indicator.

According to another embodiment of the invention, a PTI as defined above is disclosed, comprising equipment from such as medical, electrical, transmitting, lighting, monitoring, heating, ventilating, viewing, etc., wherein the equipment is interconnected to the PTI.

According to another embodiment of the invention, a PTI as defined above is disclosed, wherein the disclosed equipment is located at single or multiple locations of the PTI.

According to another embodiment of the invention, a PTI as defined above is disclosed, wherein the indicator is selected from a group consisting of: audible indicators, visual indicators, sensible indicators, and any combination thereof.

According to another embodiment of the invention, a PTI as defined above is disclosed, comprising an alarm system, wherein the alarm system is interconnected to the user interface.

According to another embodiment of the invention, a PTI as defined above is disclosed, comprising an alarm system, wherein the alarm system responds to predetermined values.

According to another embodiment of the invention, a PTI as defined above is disclosed, comprising alarm indicators, wherein the alarm indicator is selected from a group consisting of: audible indicators, visual indicators, sensible indicators and any combination thereof.

According to another embodiment of the invention, a PTI as defined above is disclosed, comprising a CPU, wherein the CPU is interconnected to the user interface.

According to another embodiment of the invention, a PTI as defined above is disclosed, wherein the CPU is interconnected to sensing equipment, medical equipment, power supply and any combination thereof.

According to another embodiment of the invention, a PTI as defined above is disclosed, wherein the derivate data from the sensing equipment and electrical equipment is transferable to other devices selected from a group consisting of: medical, monitoring, CPU, user interface, control unit, indicators and any combination thereof.

According to another embodiment of the invention, a PTI as defined above is disclosed, wherein the CPU receives, analyses, transfers and any combination thereof, data received disclosed equipment.

According to another embodiment of the invention, a PTI as defined above is disclosed, wherein the derivate data is transferable in a manner selected from a group consisting of:

conducting wires, optical fibers, wireless communication channels and any combination thereof.

According to another embodiment of the invention, a PTI as defined above is disclosed, comprising a thermo regulating vent, wherein this vent is specified in patent 61/893,959 US dated 22 Oct. 2013 and is incorporated herein in its entirety.

According to another embodiment of the invention, a PTI as defined above is disclosed, comprising at least one user interface, wherein at least one user interfaces is located at a defined area of the incubator, so that it is accessible when the PTI is in the MRD open bore.

According to another embodiment of the invention, a PTI as defined above is disclosed, comprising an envelope, wherein the envelope is configured to house at least one reversibly connectable module selected from a group consisting of: a temperature regulating vent module, a venting module, a user interface module, a control unit module, at least one life support system module, a monitoring module, a sensor module, and any combination thereof.

According to another embodiment of the invention, a PTI as defined above is disclosed, wherein at least one reversibly connectable module is connectable at a location, relative to the envelope, selected from a group consisting of: top, bottom, side, back, front and any combination thereof.

According to another embodiment of the invention, a PTI as defined above is disclosed, wherein the PTI is configured to reduce the noise within the inner volume, in a predefined sound characteristic selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a PTI as defined above is disclosed, wherein the PTI is configured to reduce the noise by at least one selected from a group consisting of: sound level reduction, sound reflections reduction, sound reverberation reduction, sound diffusion, altered sound signature, and any combination thereof.

The PTI of claim 1, wherein the PTI is configured to change at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

According to another embodiment of the invention, A PTI as defined above is disclosed, wherein the envelope comprises at least one sound reflector configured to direct the noise to a selected from a group consisting of: at least one absorptive surface, at least one sound diffuser, at least one sound baffle, at least one reflective surface, at least one resonator, at least one sound shield, a location directed away from at least a portion of the patient, and any combination thereof.

According to another embodiment of the invention, a PTI as defined above is disclosed, wherein the sound signature, is selected from a group consisting of: configurable by the user, predefined, automatically adjustable in reference to the neonate's life parameters, and any combination thereof.

According to another embodiment of the invention, a PTI as defined above is disclosed, wherein the envelope further comprises at least one selected from a group consisting of: a sound absorptive material, a resonator, a sound shield, a bass trap, a sound baffle, a diffuser, an insulation padding, a sound reflector, a sound muffler, an active sound cancellation device, and any combination thereof, configured to change the sound signature reaching the patient.

According to another embodiment of the invention, a PTI as defined above is disclosed, wherein the envelope comprises at least a portion of a material selected from a group consisting of: at least one sealing material, at least one sound absorbent material, at least one vibration absorbing material, and any combination thereof.

According to another embodiment of the invention, a PTI as defined above is disclosed, wherein at least a portion of the envelope comprises n layers; further wherein each of the n layers comprising an inner side towards the inner volume, and an opposite outer side facing towards the environment.

According to another embodiment of the invention, a PTI as defined above is disclosed, wherein each of the n layers comprising a predefined Noise Reduction Coefficient (NRC) value, Sound Transmission Class (STC) value, or both; further wherein the NRC value, STC value, or both, can be equal or different for the each of one of n layers.

According to another embodiment of the invention, a PTI as defined above is disclosed, wherein the n layers comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein $dS$ of the PTI equals $S_1$-$Sn$, and $S_1$-$Sn < S_1$.

According to another embodiment of the invention, a PTI as defined above is disclosed, wherein the n layers comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein $dS$ of the PTI equals $S_1$-$Sn$, and $S_1$-$Sn < S_1$.

According to another embodiment of the invention, a PTI as defined above is disclosed, wherein the PTI further comprising: (a) a space, $S_{1-n}$, between at least two the of n layers; (b) $STC_1$ (sound transmission class) value, measured for the layers $_{1-n}$; and, (c) reversible mobilization means, connected to at least one of the n layers, configured to mobilize at least one of the n layers, having a space $S_{1-n}$ between at least two of n layers such that a space $S_{1-n,a}$ and $STC_2$ value measured for the layers $_{1-n}$ are provided; where $S_{1-n} < S_{1n,a}$ and where $STC_1 < STC_2$.

According to another embodiment of the invention, a PTI as defined above is disclosed, wherein the envelope is configured to reduce reverberation of sound, reflections of sound, or both within the inner volume, by means of at least one selected from a group consisting of; absorptive material, a sound baffle, a sound diffuser, a sound resonator, a sound shield, and any combination thereof.

According to another embodiment of the invention, a PTI as defined above is disclosed, characterized by an elongated shape, having a main longitudinal axis with a proximal end and an opposite distal end; the PTI further comprising in at least one of the ends, a temperature regulating vent (TRV); the TRV is adapted to stream air from the end towards the opposite end substantially along the axis; and is configured, by means of size and shape, to accommodate the patient in parallel to the axis; further wherein the TRV is a module selected from a group consisting of at least one first venting module, at least one first heating/cooling module, at least one filter located adjacently to either the first venting module or the first heating/cooling module, at least one humidifying module and any combination thereof.

According to one embodiment of the present invention, a standard of care protocol for MRI of patients, comprising steps of: (a) obtaining a PTI suitable for magnetic resonance imaging device (MRD) with an open bore, the incubator comprising an inner volume having a first set of dimensions, the inner volume is adapted by means of shape and size to accommodate the patient, the inner volume further is covered by an envelope having a second set of dimensions, adapted by shape and size to be temporarily introduced within the open bore; when at least a portion of the envelope comprises MRI-safe thermo-isolating and noise reducing foam, (b) confining the compartment from its environment; (c) placing the patient into enveloped inner volume; and (d) introducing the incubator into MRI open bore and imaging; wherein at least one of the following is held true: (a) the sound pressure measured inside the PTI does not exceed a maximum level of 60 dB; and the sound level in the inner volume of the PTI compartment would be at least 10 dB lower than the sound level outside this compartment; (b) the sound pressure measured inside the PTI does not exceed a maximum level of 45 dB; and the sound level in the inner volume of the PTI compartment would be at least 10 dB lower than the sound level outside this compartment; (c) the average value of salivary cortisol level index from noise derived stress of patient when utilizing the PTI during MRI is n times lower than the average the value during MRI; n is equal or greater than 1.05; (d) the average number of movements per minute of patient when utilizing the PTI during MRI is m times lower than the average number of movements per minute of the patient; m is equal or greater than 1.05; (e) the average number of MRI repetitions per patient is p times lower when utilizing the PTI than the average number of MRI repetitions during MRI of patients; p is equal or greater than 1.05; (f) the average value of salivary cortisol level index from open space related stress of patient when utilizing the PTI during MRI is q times lower than the average value during MRI; q is equal or greater than 1.05; (g) the temperature of the inner volume of the PTI is at the most 2° C. different than the control temperature of 36° C.; (h) the $O_2$ concentration within the PTI does not fall below 30 vol. %, and does not exceed 40 vol. %; (i) the $CO_2$ concentration within the PTI does not exceed 4%; (j) the air velocity over the mattress within the PTI does not exceed 0.35 m/s; (k) the average humidity levels of the inner volume of the PTI are maintained for the duration of MRI as medically predetermined by medical personal at levels of up to 85%; (l) the PTI will continue to be used safely in occurrence of a leakage of up to 200 ml deposited in the compartment of the PTI; (m) the PTI will remain stable when tilted 10° in normal use and when tilted 20° during transportation; (o) the PTI will not tip over when the force is 100 N or less; (p) the average number of patients MRI related fall incidents when utilizing the PTI is r times lower than the average of patients MRI related fall incidents; r is equal or greater than 1.05; (q) the average number of patient infections acquired that is MRI associated, when utilizing the PTI, is s times lower than the average number of infections acquired by patients that is MRI associated; s is equal or greater than 1.05; (r) the average number of MRI associated patient's health complications when utilizing the PTI is t times lower than the average number of patients' MRI associated health complications, t is equal or greater than 1.05; (s) the radiated electromagnetic fields in the inner volume of the PTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and (t) the average number of excessive heating incidents and burn incidents in association with MRD is u times lower when utilizing the PTI; u is equal or greater than 1.05.

According to one embodiment of the present invention, a method of magnetic resonance imaging of patients comprising steps of: (a) obtaining a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam; (b) placing the patient into the enveloped inner volume; and, (c) introducing the PTI into the MRI open bore and imaging.

According to another embodiment of the invention, a method as defined above is disclosed, additionally comprising a step of obtaining the envelope further comprising at least a portion of fire retardant materials.

According to another embodiment of the invention, a method as defined above is disclosed, additionally comprising a step of obtaining an inner volume envelope from a selected group varying in means of size and shape to fit the patient.

According to another embodiment of the invention, a method as defined above is disclosed, additionally comprising a step of obtaining the envelope further comprising at least one opening.

According to another embodiment of the invention, a method as defined above is disclosed, additionally comprising at least one of the following steps: (a) obtaining the envelope in which the opening further comprises at least one sound attenuating means configured to muffle the sound passing through the opening, and muffling at least partially the sound; (b) obtaining the envelope in which the opening is adapted by means of size and shape for the passage of equipment selected from a group consisting of: tubing, life supporting, monitoring, sensing, temperature maintaining, ventilating and any combination thereof; and, passing at least a portion of the equipment form the environment to the inner volume; (c) obtaining the envelope in which the opening is adapted by means of size and shape to allow passage of a handler's hand, and reversibly passing a handler's hand through the opening.

According to another embodiment of the invention, a method as defined above is disclosed, additionally comprising a step of configuring the envelope to providing at least one open position for accommodating the patient, and at least one closed position for at least partially confining the patient within the inner volume, and accommodating or confining the patient.

According to another embodiment of the invention, a method as defined above is disclosed, additionally comprising a step of securing configured closed position of the envelope.

According to another embodiment of the invention, a method as defined above is disclosed, additionally comprising a step of obtaining the envelope further comprising a quick release mechanism enabling rapid access to a patient within the inner volume, and operating the quick release mechanism.

According to another embodiment of the invention, a method as defined above is disclosed, additionally comprising a step of obtaining the envelope further comprising at least a portion of at least partially transparent material, wherein the transparent material enables at least a part of the patient to be observed visually, and viewing the patient.

According to another embodiment of the invention, a method as defined above is disclosed, additionally comprising at least one of the following steps: (a) obtaining the envelope further configured to separate patient tissues from coming into contact with the MRD bore; (b) obtaining the envelope further comprising the inner volume facing shape selected from a group consisting of: patient ergonomic, none ergonomic, patient movement restrictive shape, and any combination thereof; and, (c) obtaining the envelope further defined by means of size and shape for enabling the placement of the patient's body such that the body does not form electrically conducting loops.

According to another embodiment of the invention, a method as defined above is disclosed, additionally comprising a step of placing the patient in a compartment fit by dimensions of size and shape to accommodate and restrict movements of the patient.

According to another embodiment of the invention, a method as defined above is disclosed, additionally comprising a step of obtaining the envelope further comprising at least one sensor configured to sense at least one parameter selected from a group consisting of: temperature, humidity, $O_2$ concentration, $CO_2$ concentration, $O_2$ concentration, sound level, sound frequency, sound direction, sound amplitude, sound tone, sound speed, vibration, movement, drift, light, PTI configuration, PTI structural integrity, PTI lock configuration and any combination thereof, and sensing by the sensor.

According to another embodiment of the invention, a method as defined above is disclosed, additionally comprising a step of receiving input from user interface, enabling surveillance of the patient.

According to another embodiment of the invention, a method as defined above is disclosed, additionally comprising a step of coupling medical equipment to the incubator.

According to another embodiment of the invention, a method as defined above is disclosed, additionally comprising a step of obtaining the envelope further configured to house at least one reversibly connectable module selected from a group consisting of: a temperature regulating vent module, a venting module, a user interface module, a control unit module, at least one life support system module, a monitoring module, a sensor module, and any combination thereof, and reversibly connect at least one aid module.

According to another embodiment of the invention, a method as defined above is disclosed, additionally comprising a step of connecting at least one reversibly connectable module at a location, relative to the envelope, selected from a group consisting of: top, bottom, side, back, front and any combination thereof.

According to another embodiment of the invention, a method as defined above is disclosed, additionally comprising a step of securing the incubator to defined patient location at MRD inner bore.

According to another embodiment of the invention, a method as defined above is disclosed, additionally comprising a step of disposing at least a part of the incubator, following the end of use.

According to another embodiment of the invention, a method as defined above is disclosed, additionally comprising a step of configuring the PTI to reduce the noise within the inner volume, in a predefined sound characteristic selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a method as defined above is disclosed, additionally comprising a step of reducing the noise within the inner volume, by at least one selected from a group consisting of: sound level reduction, sound reflections reduction, sound reverberation reduction, sound diffusion, altered sound signature, and any combination thereof.

According to another embodiment of the invention, a method as defined above is disclosed, additionally comprising a step of changing at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

According to another embodiment of the invention, a method as defined above is disclosed, additionally comprising a step of selecting the sound signature from a group consisting of: configurable by the user, predefined, automatically adjustable in reference to the neonate's life parameters, and any combination thereof.

According to another embodiment of the invention, a method as defined above is disclosed, additionally comprising a step of obtaining the envelope further comprising at least one selected from a group consisting of: a sound absorptive material, a resonator, a sound shield, a bass trap, a sound baffle, a diffuser, an insulation padding, a sound reflector, a sound muffler, an active sound cancellation device, and any combination thereof, configured to change the sound signature reaching the patient.

According to another embodiment of the invention, a method as defined above is disclosed, additionally comprising a step of obtaining the envelope further comprising at least a portion of a material selected from a group consisting of: at least one sealing material, at least one sound absorbent material, at least one vibration absorbing material, and any combination thereof.

According to another embodiment of the invention, a method as defined above is disclosed, additionally comprising a step of obtaining the envelope in which at least a portion comprising n layers; further wherein each of the n layers comprising an inner side towards the inner volume, and an opposite outer side facing towards the environment.

According to another embodiment of the invention, a method as defined above is disclosed, additionally comprising a step of obtaining the envelope comprising n layers, each of the n layers comprising a predefined Noise Reduction Coefficient (NRC) value, Sound Transmission Class (STC) value, or both; further selecting each the layer comprising equal or different the NRC value, STC value, or both, for the each of one of n layers.

According to another embodiment of the invention, a method as defined above is disclosed, additionally comprising a step of obtaining the envelope comprising the n layers further comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein dS of the PTI equals $S_1$-$Sn$, and $S_1$-$Sn$<$S_1$.

According to another embodiment of the invention, a method as defined above is disclosed, additionally comprising a step of obtaining the envelope comprising the n layers further comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein dS of the PTI equals $S_1$-$Sn$, and $S_1$-$Sn$<$S_1$.

According to another embodiment of the invention, a method as defined above is disclosed, additionally comprising a step of obtaining the envelope further comprising: (a) a space, $S_{1-n}$, between at least two the of n layers; (b) STC (sound transmission class) value, measured for the layers $_{1-n}$; and, (c) reversible mobilization means, connected to at least one of the n layers, configured to mobilize at least one of the n layers, having a space $S_{1-n}$ between at least two of n layers such that a space $S_{1-n,a}$ and $STC_2$ value measured for the layers $_{1-n}$ are provided; where $S_{1-n}$<$S_{1n,a}$ and where $STC_1$<$STC_2$, and reversibly mobilizing at least one layers.

According to another embodiment of the invention, a method as defined above is disclosed, additionally comprising a step of obtaining the envelope further configured to reduce reverberation of sound, reflections of sound, or both within the inner volume, by means of utilizing at least one selected from a group consisting of: absorptive material, a sound baffle, a sound diffuser, a sound resonator, a sound shield, and any combination thereof.

According to another embodiment of the invention, a method as defined above is disclosed, additionally comprising the following steps: (a) obtaining the envelope further characterized by an elongated shape, having a main longitudinal axis with a proximal end and an opposite distal end; the PTI further comprising in at least one of the ends, a temperature regulating vent (TRV); the TRV is adapted to stream air from the end towards the opposite end substantially along the axis; and is configured, by means of size and shape, to accommodate the patient in parallel to the axis; (b) selecting the TRV from a group consisting of at least one first venting module, at least one first heating/cooling module, at least one filter located adjacently to either the first venting module or the first heating/cooling module, at least one humidifying module and any combination thereof; and, (c) operating the TRV, thereby preforming at least one of the following: venting, heating, cooling, filtering, humidifying, the air within the inner volume.

According to one embodiment of the invention a method of manufacturing a patient transport incubator (PTI) suitable for MRI device having an open bore; the PTI comprises an inner volume having a first set of dimensions, adapted by means of shape and size to accommodate a patient, the inner volume is further covered by an envelope having a second set of dimensions, adapted by means of shape and size to be temporarily introduced within the open bore; wherein at least a portion of the envelope comprises MRI safe thermo-isolating and noise reducing foam, comprising steps of: (a) defining dimensions of inner volume to accommodate the patient; (b) defining dimension adapted by shape and size for the envelope to be temporarily introduced within the MRI open bore; and (c) forming envelope separating inner volume from its environment; wherein at least a portion of the envelope comprises MRI safe thermo-isolating noise reducing foam, separating the inner volume from its environment.

According to another embodiment of the invention, a method as defined above is disclosed, additionally comprising a step of integrating at least a portion of the foam with fire retardant materials.

According to another embodiment of the invention, a method as defined above is disclosed, additionally comprising a step of connecting at least two parts in order to form the envelope separating inner volume from its environment.

According to another embodiment of the invention, a method as defined above is disclosed, additionally comprising a step of forming at least a portion of the envelope in a multi-layer construction.

According to another embodiment of the invention, a method as defined above is disclosed, additionally comprising a step of defining a plurality of dimensions for the inner volume to accommodate various size and shape patients.

According to another embodiment of the invention, a method as defined above is disclosed, additionally comprising a step of defining dimensions of inner volume to accommodate the patient forming at least a portion of the envelope in a shape creating an ergonomic patient space.

According to another embodiment of the invention, a method as defined above is disclosed, additionally comprising a step of defining the dimensions of the envelope parts to be adapted to be ergonomic to the handler.

According to another embodiment of the invention, a method as defined above is disclosed, additionally comprising a step of defining the dimensions of the envelope to be adapted by means of size and shape to separates the patient's tissues from coming into contact with the MRD bore.

According to another embodiment of the invention, a method as defined above is disclosed, additionally comprising a step of defining the dimensions of the envelope to be adapted by means of size and shape to place the patient's body so that it does not form conducting loops.

According to another embodiment of the invention, a method as defined above is disclosed, additionally comprising a step of forming at least a portion of the envelope foam by means selected from a group consisting of: open-molding, closed-molding injection, vacuum forming, extruding, expanding, casting, stretching, sheet assembling, foaming, compositing and any combination thereof.

According to another embodiment of the invention, a method as defined above is disclosed, additionally comprising a step of further forming at least a part of the envelope by surface modifications selected from a group consisting of: cleaning, sterilizing, smoothing, adding texture, coloring, covering, typing, adhering, puncturing, hammering, spraying, immersing and any combination thereof.

According to another embodiment of the invention, a method as defined above is disclosed, additionally comprising a step of creating at least one opening in the incubator.

According to another embodiment of the invention, a method as defined above is disclosed, additionally comprising a step of creating a space fitting by dimensions of size and shape to permit passage of equipment selected from a group of: medical, electrical, data transferring, sensing, ventilating, heating, viewing, monitoring and any combination thereof.

According to another embodiment of the invention, a method as defined above is disclosed, additionally comprising a step of defining the connection areas between the envelope by means of location, material, shape and size to isolate the inner volume of the envelope from the outside conditions selected from a group consisting of: temperature, humidity, sound, vibration, $O_2$ concentration, $CO_2$ concentration and any combination thereof.

According to another embodiment of the invention, a method as defined above is disclosed, additionally comprising a step of forming the envelope comprising at least one opening.

According to another embodiment of the invention, a method as defined above is disclosed, additionally comprising a step of, wherein at least one of the following holds true: (a) attaching at least one sound attenuating means configured to muffle the sound passing through the opening; (b) adapting the opening by means of size and shape for the passage of equipment selected from a group consisting of: tubing, life supporting, monitoring, sensing, temperature maintaining, ventilating and any combination thereof; and, (c) configuring the opening by means of size and shape to allow passage of a handler's hand.

According to another embodiment of the invention, a method as defined above is disclosed, additionally comprising a step of configuring the envelope for at least one open position for accommodating the patient, and at least one closed position for at least partially confining the patient within the inner volume.

According to another embodiment of the invention, a method as defined above is disclosed, additionally comprising a step of integrating a quick release mechanism enabling rapid access to the patient within inner volume.

According to another embodiment of the invention, a method as defined above is disclosed, additionally comprising a step of integrating a quick release mechanism enabling rapid release of the incubator from MRD open bore.

According to another embodiment of the invention, a method as defined above is disclosed, additionally comprising a step of forming at least a portion of the envelope comprising at least partially transparent material, thereby enabling at least a part of the patient to be observed visually.

According to another embodiment of the invention, a method as defined above is disclosed, additionally comprising a step of, wherein at least one of the following holds true: (a) forming the envelope configured to separating the patient tissues from coming into contact with the MRD bore; (b) selecting the envelope inner volume facing shape from a group consisting of: patient ergonomic, none ergonomic, patient movement restrictive shape, and any combination thereof; and, (c) defining the envelope by means of size and shape for enabling placement of the patient's body such that the body does not form electrically conducting loops.

According to another embodiment of the invention, a method as defined above is disclosed, additionally comprising a step of attaching at least one sensor to the envelope, and configuring the sensor to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

According to another embodiment of the invention, a method as defined above is disclosed, additionally comprising a step of configuring the envelope to house at least one reversibly connectable module selected from a group consisting of: a temperature regulating vent module, a venting module, a user interface module, a control unit module, at least one life support system module, a monitoring module, a sensor module, and any combination thereof.

According to another embodiment of the invention, a method as defined above is disclosed, additionally comprising a step of constructing a separate module of user interface.

According to another embodiment of the invention, a method as defined above is disclosed, additionally comprising a step of interconnecting user interface module to the incubator.

According to another embodiment of the invention, a method as defined above is disclosed, additionally comprising a step of connecting sensing equipment from a selected group consisting of: temperature, humidity, gas concentrations, sound levels, vibrations, drift, light, respiration, cardiac function, blood oxygenation, neurological activity, electricity, radio frequency, data transfer, opened or closed state of incubator envelope, structural integrity of incubator, structural integrity of interconnected parts, general function of incubator and any combination thereof to the incubator.

According to another embodiment of the invention, a method as defined above is disclosed, additionally comprising a step of connecting user interface to an item selected from a group consisting of: medical equipment, sensing equipment, electrical equipment, monitoring equipment, control unit, CPU, audio indicator, visual indicator, sensing indicator, alarm system, power supply and any combination thereof.

According to another embodiment of the invention, a method as defined above is disclosed, additionally comprising a step of creating at least one reversible connection for at a location, relative to the envelope, selected from a group consisting of: top, bottom, side, back, front and any combination thereof.

According to another embodiment of the invention, a method as defined above is disclosed, additionally comprising a step of configuring the PTI to reduce the noise within the inner volume, in a predefined sound characteristic, and selecting the sound characteristic from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a method as defined above is disclosed, additionally comprising a step of selecting at least one noise parameter to be reduced from a group consisting of: sound level reduction, sound reflections reduction, sound reverberation reduction, sound diffusion, altered sound signature, and any combination thereof.

According to another embodiment of the invention, a method as defined above is disclosed, additionally comprising a step of selecting at least one sound characteristic reaching the inner volume from the environment from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature, to be changed by the PTI.

According to another embodiment of the invention, a method as defined above is disclosed, additionally comprising a step of selecting the sound signature from a group consisting of: configurable by the user, predefined, automatically adjustable in reference to the patient's life parameters, and any combination thereof.

According to another embodiment of the invention, a method as defined above is disclosed, additionally comprising a step of including at least one means selected from a group consisting of: a sound absorptive material, a resonator, a sound shield, a bass trap, a sound baffle, a diffuser, an insulation padding, a sound reflector, a sound muffler, and any combination thereof, configured to changing the sound signature reaching the patient.

According to another embodiment of the invention, a method as defined above is disclosed, additionally comprising a step of forming at least a portion of the envelope of a material selected from a group consisting of: at least one sealing material, at least one sound absorbent material, at least one vibration absorbing material, and any combination thereof.

According to another embodiment of the invention, a method as defined above is disclosed, additionally comprising a step of forming at least a portion of the envelope comprising n layers; further wherein each of the n layers comprising an inner side towards the inner volume, and an opposite outer side facing towards the environment.

According to another embodiment of the invention, a method as defined above is disclosed, additionally comprising a step of forming each of the n layers comprising a predefined Noise Reduction Coefficient (NRC) value, Sound Transmission Class (STC) value, or both; further wherein the NRC value, STC value, or both, can be equal or different for the each of one of n layers.

According to another embodiment of the invention, a method as defined above is disclosed, additionally comprising a step of forming the n layers comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising a step of forming the n layers comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising the following steps: (a) forming the envelope further comprising a space, $S_{1-n}$, between at least two the of n layers; (b) configuring at least one $STC_1$ (sound transmission class) value, measured for the layers $_{1-n}$; and, (c) connecting reversible mobilization means, connected to at least one of the n layers, configured to mobilizing at least one of the n layers, having a space $S_{1-n}$ between at least two of n layers such that a space $S_{1-n,a}$ and $STC_2$ value measured for the layers $_{1-n}$ are provided; where $S_{1-n}<S_{1n,a}$ and where $STC_1<STC_2$.

According to another embodiment of the invention, a method as defined above is disclosed, additionally comprising a step of configuring the envelope to reduce reverberation of sound, reflections of sound, or both within the inner volume, by means of at least one selected from a group consisting of: absorptive material, a sound baffle, a sound diffuser, a sound resonator, a sound shield, an active sound cancellation device and any combination thereof.

According to another embodiment of the invention, a method as defined above is disclosed, additionally comprising the following steps: (a) forming the envelope further characterized by an elongated shape, having a main longitudinal axis with a proximal end and an opposite distal end; (b) connecting a temperature regulating vent (TRV) to the PTI in at least one of the ends; (c) configuring the TRV to stream air from the end towards the opposite end substantially along the axis; (d) configuring the envelope, by means of size and shape, to accommodate the patient in parallel to the axis; and, (e) selecting the TRV from a group consisting of at least one first venting module, at least one first heating/cooling module, at least one filter located adjacently to either the first venting module or the first heating/cooling module, at least one humidifying module and any combination thereof.

According to one embodiment of the present invention, a patient transport incubator (PTI) suitable for magnetic resonance imaging device (MRD) is provided. The MRD, having an open bore, the incubator comprising an inner volume, having a first set of dimensions, the inner volume is adapted by means of shape and size to accommodate at least a portion of MRI-compatible neonate's cradle, as depicted in patent 226488 IL, dated 21 May 2013 and is incorporated in its entirety; the inner volume further is covered by an envelope having a second set of dimensions, adapted by shape and size to be temporarily introduced within the open bore; wherein at least a portion of the envelope comprises thermo-isolating MRI safe, non-interfering noise reducing foam, separating the inner volume from its environment.

According to another embodiment of the invention, A PTI as defined above is disclosed, comprising at least two connected parts, wherein the parts are connected by means such as hinge, joint, hook, link, bridge, clamp, bond, bracket, clasp, lock, snap, brace, grip, juncture, interweave, threading, etc.

According to another embodiment of the invention, a PTI as defined above is disclosed, wherein the open position is achieved by moving at least a part of the envelope relative to another part of the envelope that remains in a fixed position. This movement enables the envelope parts be to completely separate or remain connected in at least a portion of the envelope.

According to another embodiment of the invention, a PTI as defined above is disclosed, wherein the connection between the envelope parts is defined by means of location, material and shape to better isolate the inner volume of the envelope from the outside conditions selected from a group consisting of: temperature, sound, vibration and any combination thereof.

According to another embodiment of the invention, a PTI as defined above is disclosed, wherein the envelope is formed in at least one of a plurality of shapes such as cylindered, polygonal, polymorphic, symmetrical, none symmetrical, concave, ergonomic, etc.

According to another embodiment of the invention, a PTI as defined above is disclosed, wherein a mechanism attaches the PTI to MRI-compatible neonate's cradle; The attaching mechanism operates by: belting, screwing, hammering, fitting, sliding, tracking, latching, locking, joining, affixing, embedding, interweaving, clamping, coupling, locking, implanting, attaching, linking, adhering, stamping, covering, layering, connecting, interconnecting, hooking, inserting, engulfing etc. Further this attachment is a fast release mechanism, enabling fast access to the MRI-compatible cradle within.

According to another embodiment of the invention, a PTI as defined above is disclosed, comprising at least one user interface, wherein at least one user interfaces is located at a defined area of the incubator, so that it is accessible when the PTI is in the MRD open bore.

According to another embodiment of the invention, a PTI as defined above is disclosed, comprising sensing equipment wherein the equipment is connected embedded, integrated, layered, interconnected, fitted, placed, interweaved, adhered, implanted, nested, etc. to at least a portion of the PTI.

According to another embodiment of the invention, a PTI as defined above is disclosed, comprising sensing equipment, further comprising at least one indicator, wherein the equipment responds to at least one signal by transmitting data to at least one indicator.

According to another embodiment of the invention, a PTI as defined above is disclosed, comprising equipment from such as medical, electrical, transmitting, lighting, monitoring, heating, ventilating, viewing, etc., wherein the equipment is interconnected to the PTI.

According to another embodiment of the invention, a PTI as defined above is disclosed, wherein the disclosed equipment is located at single or multiple locations of the PTI.

According to another embodiment of the invention, a PTI as defined above is disclosed, wherein the indicator is selected from a group consisting of: audible indicators, visual indicators, sensible indicators, and any combination thereof.

According to another embodiment of the invention, a PTI as defined above is disclosed, comprising an alarm system, wherein the alarm system is interconnected to the user interface.

According to another embodiment of the invention, a PTI as defined above is disclosed, comprising an alarm system, wherein the alarm system responds to predetermined values.

According to another embodiment of the invention, a PTI as defined above is disclosed, comprising alarm indicators, wherein the alarm indicator is selected from a group consisting of: audible indicators, visual indicators, sensible indicators and any combination thereof.

According to another embodiment of the invention, a PTI as defined above is disclosed, comprising a CPU, wherein the CPU is interconnected to the user interface.

According to another embodiment of the invention, a PTI as defined above is disclosed, wherein the CPU is interconnected to sensing equipment, medical equipment, power supply and any combination thereof.

According to another embodiment of the invention, a PTI as defined above is disclosed, wherein the derivate data from the sensing equipment and electrical equipment is transferable to other devices selected from a group consisting of: medical, monitoring, CPU, user interface, control unit, indicators and any combination thereof.

According to another embodiment of the invention, a PTI as defined above is disclosed, wherein the CPU receives, analyses, transfers and any combination thereof data received disclosed equipment.

According to another embodiment of the invention, a PTI as defined above is disclosed, wherein the derivate data is transferable in a manner selected from a group consisting of: copper wires, optical fibers, wireless communication channels and any combination thereof.

According to another embodiment of the invention, a PTI as defined above is disclosed, comprising an enveloped inner volume, wherein at least a portion of the envelope is integrated with fire retardant materials.

According to another embodiment of the invention, a PTI as defined above is disclosed, wherein the envelope comprises at least one opening.

According to another embodiment of the invention, a PTI as defined above is disclosed, wherein at least one of the following holds true: (a) the opening further comprises at least one sound attenuating means configured to muffle the sound passing through the opening; (b) the opening is adapted by means of size and shape for the passage of equipment selected from a group consisting of: tubing, life supporting, monitoring, sensing, temperature maintaining, ventilating and any combination thereof; and, (c) the opening is adapted by means of size and shape to allow passage of a handler's hand.

According to another embodiment of the invention, a PTI as defined above is disclosed, comprising an envelope, wherein the envelope is configured for at least one open position for accommodating the MRI-compatible neonate's cradle, and at least one closed position configured to at least partially confine the MRI-compatible neonate's cradle within the inner volume.

According to another embodiment of the invention, a PTI as defined above is disclosed, wherein the envelope comprises a quick release mechanism enabling rapid access to a patient within the inner volume.

According to another embodiment of the invention, a PTI as defined above is disclosed, comprising at least a portion of at least partially transparent material, wherein the transparent material enables at least a part of the patient to be observed visually.

According to another embodiment of the invention, a PTI as defined above is disclosed, wherein at least one of the following holds true: (a) the envelope separates patient tissues from coming into contact with the MRD bore; (b) the envelope shape facing the inner volume is selected from a group consisting of: patient ergonomic, none ergonomic, patient movement restrictive shape, and any combination thereof; and, (c) the envelope is defined by means of size and shape to enable the placement of the patient's body such that the body does not form electrically conducting loops.

According to another embodiment of the invention, a PTI as defined above is disclosed, comprising at least one sensor configured to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

According to another embodiment of the invention, a PTI as defined above is disclosed, comprising an envelope, wherein the envelope is configured to house at least one reversibly connectable module selected from a group consisting of: a temperature regulating vent module, a venting module, a user interface module, a control unit module, at least one life support system module, a monitoring module, a sensor module, and any combination thereof.

According to another embodiment of the invention, a PTI as defined above is disclosed, wherein at least one reversibly connectable module is connectable at a location, relative to the envelope, selected from a group consisting of: top, bottom, side, back, front and any combination thereof.

According to another embodiment of the invention, a PTI as defined above is disclosed, wherein the PTI is configured to reduce the noise within the inner volume, in a predefined sound characteristic selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a PTI as defined above is disclosed, wherein the PTI is configured to reduce the noise by at least one selected from a group consisting of: sound level reduction, sound reflections reduction, sound reverberation reduction, sound diffusion, altered sound signature, and any combination thereof.

According to another embodiment of the invention, a PTI as defined above is disclosed, wherein the PTI is configured to change at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

According to another embodiment of the invention, a PTI as defined above is disclosed, wherein the sound signature, is selected from a group consisting of: configurable by the user, predefined, automatically adjustable in reference to the neonate's life parameters, and any combination thereof.

According to another embodiment of the invention, a PTI as defined above is disclosed, wherein the envelope further comprises at least one selected from a group consisting of: a sound absorptive material, a resonator, a sound shield, a bass trap, a sound baffle, a diffuser, an insulation padding, a sound reflector, a sound muffler, and any combination thereof, configured to change the sound signature reaching the patient.

According to another embodiment of the invention, a PTI as defined above is disclosed, wherein the envelope comprises at least a portion of a material selected from a group consisting of: at least one sealing material, at least one sound absorbent material, at least one vibration absorbing material, and any combination thereof.

According to another embodiment of the invention, a PTI as defined above is disclosed, wherein at least a portion of the envelope comprises n layers; further wherein each of the n layers comprising an inner side towards the inner volume, and an opposite outer side facing towards the environment.

According to another embodiment of the invention, a PTI as defined above is disclosed, wherein each of the n layers comprising a predefined Noise Reduction Coefficient (NRC) value, Sound Transmission Class (STC) value, or both; further wherein the NRC value, STC value, or both, can be equal or different for the each of one of n layers.

According to another embodiment of the invention, a PTI as defined above is disclosed, wherein the n layers comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein $dS$ of the PTI equals $S_1$-$Sn$, and $S_1$-$Sn < S_1$.

According to another embodiment of the invention, a PTI as defined above is disclosed, wherein the n layers comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein $dS$ of the PTI equals $S_1$-$Sn$, and $S_1$-$Sn < S_1$.

According to another embodiment of the invention, a PTI as defined above is disclosed, wherein the PTI further comprising: (a) a space, $S_{1-n}$, between at least two the of n layers; (b) $STC_1$ (sound transmission class) value, measured for the layers $_{1-n}$; and, (c) reversible mobilization means, connected to at least one of the n layers, configured to mobilize at least one of the n layers, having a space $S_{1-n}$ between at least two of n layers such that a space $S_{1-n,a}$ and $STC_2$ value measured for the layers $_{1-n}$ are provided; where $S_{1-n} < S_{1n,a}$ and where $STC_1 < STC_2$.

According to another embodiment of the invention, a PTI as defined above is disclosed, wherein the envelope is configured to reduce reverberation of sound, reflections of sound, or both within the inner volume, by means of at least one selected from a group consisting of: absorptive material, a sound baffle, a sound diffuser, a sound resonator, a sound shield, an active sound cancellation device and any combination thereof.

According to another embodiment of the invention, a PTI as defined above is disclosed, characterized by an elongated shape, having a main longitudinal axis with a proximal end and an opposite distal end; the PTI further comprising in at least one of the ends, a temperature regulating vent (TRV); the TRV is adapted to stream air from the end towards the opposite end substantially along the axis; and is configured, by means of size and shape, to accommodate the patient in parallel to the axis; further wherein the TRV is a module selected from a group consisting of at least one first venting module, at least one first heating/cooling module, at least one filter located adjacently to either the first venting module or the first heating/cooling module, at least one humidifying module and any combination thereof.

According to one method of the invention a magnetic resonance imaging of patients comprising steps of: (a) obtaining a patient transport incubator (PTI) suitable for MRI device having an open bore; the PTI comprises an inner volume having a first set of dimensions, adapted by means of shape and size to accommodate at least a portion of an MRI-compatible neonate's cradle, the inner volume is further covered by an envelope having a second set of dimensions, adapted by means of shape and size to be temporarily introduced within the open bore; wherein at least a portion of the envelope comprises MRI safe thermo-isolating and noise reducing foam; (b) placing neonate into the neonate's cradle; (c) placing the neonate's cradle into the enveloped inner volume; and, (d) introducing the incubator into the MRI open bore and imaging.

According to another embodiment of the invention, a method as defined above is disclosed, additionally comprising a step of obtaining the envelope further comprising at least a portion of fire retardant materials.

According to another embodiment of the invention, a method as defined above is disclosed, additionally comprising a step of obtaining the envelope further comprising at least one opening.

According to another embodiment of the invention, a method as defined above is disclosed, additionally comprising at least one of the following steps: (a) obtaining the envelope in which the opening further comprises at least one sound attenuating means configured to muffle the sound passing through the opening, and muffling at least partially the sound; (b) obtaining the envelope in which the opening is adapted by means of size and shape for the passage of equipment selected from a group consisting of: tubing, life supporting, monitoring, sensing, temperature maintaining, ventilating and any combination thereof; and, passing at least a portion of the equipment from the environment to the inner volume; and, (c) obtaining the envelope in which the opening is adapted by means of size and shape to allow passage of a handler's hand, and reversibly passing a handler's hand through the opening.

According to another embodiment of the invention, a method as defined above is disclosed, additionally comprising a step of configuring the envelope to providing at least one open position for accommodating the patient, and at least one closed position for to at least partially confining the patient within the inner volume, and accommodating or confining the patient.

According to another embodiment of the invention, a method as defined above is disclosed, additionally comprising a step of securing the closed position of the envelope by means of such as a lock, bar, belt, pin, hook, and etc.

According to another embodiment of the invention, a method as defined above is disclosed, additionally comprising a step of obtaining the envelope further comprising a quick release mechanism enabling rapid access to a patient within the inner volume, and operating the quick release mechanism.

According to another embodiment of the invention, a method as defined above is disclosed, additionally comprising a step of obtaining the envelope further comprising at least a portion of at least partially transparent material, wherein the transparent material enables at least a part of the patient to be observed visually, and viewing the patient.

According to another embodiment of the invention, a method as defined above is disclosed, additionally comprising at least one of the following steps: (a) obtaining the envelope further configured to separating patient tissues from coming into contact with the MRD bore; (b) obtaining the envelope further comprising the inner volume facing shape selected from a group consisting of: patient ergonomic, none ergonomic, patient movement restrictive shape, and any combination thereof; and, (c) obtaining the envelope further defined by means of size and shape for enabling the placement of the patient's body such that the body does not form electrically conducting loops.

According to another embodiment of the invention, a method as defined above is disclosed, additionally comprising a step of obtaining the envelope further comprising at least one sensor configured to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof, and sensing by the sensor.

According to another embodiment of the invention, a method as defined above is disclosed, additionally comprising a step of coupling equipment such as medical, electrical, data transferring, lighting, monitoring, heating, ventilating, viewing, etc. to the PTI.

According to another embodiment of the invention, a method as defined above is disclosed, additionally comprising a step of receiving input from user interface, enabling surveillance of the patient.

According to another embodiment of the invention, a method as defined above is disclosed, additionally comprising a step of quick releasing the MRI-compatible neonate's cradle from the PTI following need.

According to another embodiment of the invention, a method as defined above is disclosed, additionally comprising a step of obtaining the envelope further configured to house at least one reversibly connectable module selected from a group consisting of: a temperature regulating vent module, a venting module, a user interface module, a control unit module, at least one life support system module, a monitoring module, a sensor module, and any combination thereof, and reversibly connect at least one aid module.

According to another embodiment of the invention, a method as defined above is disclosed, additionally comprising a step of connecting at least one reversibly connectable module at a location, relative to the envelope, selected from a group consisting of: top, bottom, side, back, front and any combination thereof.

According to another embodiment of the invention, a method as defined above is disclosed, additionally comprising a step of configuring the PTI to reduce the noise within the inner volume, in a predefined sound characteristic selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a method as defined above is disclosed, additionally comprising a step of reducing the noise within the inner volume, by at least one selected from a group consisting of: sound level reduction, sound reflections reduction, sound reverberation reduction, sound diffusion, altered sound signature, and any combination thereof.

According to another embodiment of the invention, a method as defined above is disclosed, additionally comprising a step of changing at least one sound characteristic reaching the inner volume from the environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature.

According to another embodiment of the invention, a method as defined above is disclosed, additionally comprising a step of selecting the sound signature from a group consisting of: configurable by the user, predefined, automatically adjustable in reference to the neonate's life parameters, and any combination thereof.

According to another embodiment of the invention, a method as defined above is disclosed, additionally comprising a step of obtaining the envelope further comprising at least one selected from a group consisting of: a sound absorptive material, a resonator, a sound shield, a bass trap, a sound baffle, a diffuser, an insulation padding, a sound reflector, a sound muffler, an active sound cancellation device, and any combination thereof, configured to change the sound signature reaching the patient.

According to another embodiment of the invention, a method as defined above is disclosed, additionally comprising a step of obtaining the envelope further comprising at least a portion of a material selected from a group consisting of: at least one sealing material, at least one sound absorbent material, at least one vibration absorbing material, and any combination thereof.

According to another embodiment of the invention, a method as defined above is disclosed, additionally comprising a step of obtaining the envelope in which at least a portion comprising n layers; further wherein each of the n layers comprising an inner side towards the inner volume, and an opposite outer side facing towards the environment.

According to another embodiment of the invention, a method as defined above is disclosed, additionally comprising a step of obtaining the envelope comprising n layers, each of the n layers comprising a predefined Noise Reduction Coefficient (NRC) value, Sound Transmission Class (STC) value, or both; further selecting each the layer comprising equal or different the NRC value, STC value, or both, for the each of one of n layers.

According to another embodiment of the invention, a method as defined above is disclosed, additionally comprising a step of obtaining the envelope comprising the n layers further comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising a step of obtaining the envelope comprising the n layers further comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising a step of obtaining the envelope further comprising: (a) a space, $S_{1-n}$, between at least two the of n layers; (b) STC (sound transmission class) value, measured for the layers $_{1-n}$; and, (c) reversible mobilization means, connected to at least one of the n layers, configured to mobilize at least one of the n layers, having a space $S_1$, between at least two of n layers such that a space $S_{1-n,a}$ and $STC_2$ value measured for the layers $_{1-n}$ are provided; where $S_{1-n}$<$S_{1n,a}$ and where $STC_1$<$STC_2$, and reversibly mobilizing at least one layers.

According to another embodiment of the invention, a method as defined above is disclosed, additionally comprising a step of obtaining the envelope further configured to reduce reverberation of sound, reflections of sound, or both within the inner volume, by means of utilizing at least one selected from a group consisting of: absorptive material, a sound baffle, a sound diffuser, a sound resonator, a sound shield, and any combination thereof.

According to another embodiment of the invention, a method as defined above is disclosed, additionally comprising the following steps: (a) obtaining the envelope further characterized by an elongated shape, having a main longitudinal axis with a proximal end and an opposite distal end; the PTI further comprising in at least one of the ends, a temperature regulating vent (TRV); the TRV is adapted to stream air from the end towards the opposite end substantially along the axis; and is configured, by means of size and shape, to accommodate the patient in parallel to the axis; (b) selecting the TRV from a group consisting of at least one first venting module, at least one first heating/cooling module, at least one filter located adjacently to either the first venting module or the first heating/cooling module, at least one humidifying module and any combination thereof; and, (c) operating the TRV, thereby preforming at least one of the following: venting, heating, cooling, filtering, humidifying, the air within the inner volume.

According to one embodiment of the present invention a method of manufacturing a patient transport incubator (PTI) suitable for MRI device having an open bore; the PTI comprises an inner volume having a first set of dimensions, adapted by means of shape and size to accommodate at least a portion of an MRI-compatible neonate's cradle, the inner volume is further covered by an envelope having a second set of dimensions, adapted by means of shape and size to be temporarily introduced within the open bore; wherein at least a portion of the envelope comprises MRI safe thermo-isolating and noise reducing foam, comprising steps of: (a) defining dimensions of inner volume to accommodate at least a portion of the MRI-compatible neonate's cradle; (b) defining dimension adapted by shape and size for the envelope to be temporarily introduced within the MRI open bore when accommodating at least a portion of the MRI compatible neonate's cradle; and (c) forming the envelope separating inner volume from its environment; wherein at least a portion of the envelope comprises MRI safe, thermo-isolating, noise reducing foam, separating the inner volume from its environment.

According to another embodiment of the invention, a method as defined above is disclosed, additionally comprising a step of forming at least a portion of the envelope is integrated with fire retardant materials.

According to another embodiment of the invention, a method as defined above is disclosed, additionally comprising a step of forming the envelope comprising at least one opening.

According to another embodiment of the invention, a method as defined above is disclosed, additionally comprising a step of, wherein at least one of the following holds true: (a) attaching at least one sound attenuating means configured to muffle the sound passing through the opening; (b) adapting the opening by means of size and shape for the passage of equipment selected from a group consisting of: tubing, life supporting, monitoring, sensing, temperature maintaining, ventilating and any combination thereof; and, (d) configuring the opening by means of size and shape to allow passage of a handler's hand.

According to another embodiment of the invention, a method as defined above is disclosed, additionally comprising a step of configuring the envelope for at least one open position for accommodating the patient, and at least one closed position for at least partially confining the patient within the inner volume.

According to another embodiment of the invention, a method as defined above is disclosed, additionally comprising a step of attaching a quick release mechanism enabling rapid access to a patient within the inner volume.

According to another embodiment of the invention, a method as defined above is disclosed, additionally comprising a step of forming at least a portion of the envelope comprising at least partially transparent material, thereby enabling at least a part of the patient to be observed visually.

According to another embodiment of the invention, a method as defined above is disclosed, additionally comprising a step of, wherein at least one of the following holds true: (a) forming the envelope configured to separating the patient tissues from coming into contact with the MRD bore; (b) selecting the envelope inner volume facing shape from a group consisting of: patient ergonomic, none ergonomic, patient movement restrictive shape, and any combination thereof; and, (c) defining the envelope by means of size and shape for enabling placement of the patient's body such that the body does not form electrically conducting loops.

According to another embodiment of the invention, a method as defined above is disclosed, additionally comprising a step of attaching at least one sensor to the envelope, and configuring the sensor to sense at least one parameter selected from a group consisting of: temperature, humidity, $O_2$ concentration, $CO_2$ concentration, sound level, sound frequency, sound direction, sound amplitude, sound tone, sound speed, vibration, movement, drift, light, PTI configuration, PTI structural integrity, PTI lock configuration and any combination thereof.

According to another embodiment of the invention, a method as defined above is disclosed, additionally comprising a step of connecting at least two parts in order to form the envelope separating inner volume from its environment.

According to another embodiment of the invention, a method as defined above is disclosed, additionally comprising a step of defining the dimensions of the envelope parts to be adapted to be ergonomic to the handler.

According to another embodiment of the invention, a method as defined above is disclosed, additionally comprising a step of forming at least a portion of the envelope foam by means selected from a group consisting of: open-molding, closed-molding injection, vacuum forming, extruding, expanding, casting, stretching, sheet assembling, foaming, compositing and any combination thereof.

According to another embodiment of the invention, a method as defined above is disclosed, additionally comprising a step of further forming at least a part of the envelope by surface modifications such as cleaning, sterilizing, smoothing, adding texture, coloring, covering, typing, adhering, puncturing, hammering, spraying, immersing, etc.

According to another embodiment of the invention, a method as defined above is disclosed, additionally comprising a step of creating a space fitting by dimensions of size and shape to permit passage of equipment selected from a group of: medical, electrical, data transferring, sensing, ventilating, heating, viewing, monitoring and any combination thereof.

According to another embodiment of the invention, a method as defined above is disclosed, additionally comprising a step of defining the connection areas between the envelope by means of location, material, shape and size to isolate the inner volume of the envelope from the outside conditions such as temperature, humidity, sound, vibration, etc.

According to another embodiment of the invention, a method as defined above is disclosed, additionally comprising a step of including at least one user interface.

According to another embodiment of the invention, a method as defined above is disclosed, additionally comprising a step of constructing a separate module of user interface.

According to another embodiment of the invention, a method as defined above is disclosed, additionally comprising a step of connecting sensing equipment from a selected group consisting of: temperature, humidity, gas concentrations, sound levels, vibrations, drift, light, respiration, cardiac function, blood oxygenation, neurological activity, electricity, radio frequency, data transfer, opened or closed state of incubator envelope, structural integrity of incubator, structural integrity of interconnected parts, general function of incubator and any combination thereof to the incubator.

According to another embodiment of the invention, a method as defined above is disclosed, additionally comprising a step of connecting user interface to an item selected from a group consisting of: medical equipment, sensing equipment, electrical equipment, monitoring equipment, control unit, CPU, audio indicator, visual indicator, sensing indicator, alarm system, power supply and any combination thereof.

According to another embodiment of the invention, a method as defined above is disclosed, additionally comprising a step of integrating a quick release mechanism enabling rapid access to the MRI-compatible neonate's cradle within inner volume.

According to another embodiment of the invention, a method as defined above is disclosed, additionally comprising a step of configuring the envelope to house at least one reversibly connectable module selected from a group consisting of: a temperature regulating vent module, a venting module, a user interface module, a control unit module, at least one life support system module, a monitoring module, a sensor module, and any combination thereof.

According to another embodiment of the invention, a method as defined above is disclosed, additionally comprising a step of creating at least one reversible connection for at a location, relative to the envelope, selected from a group consisting of: top, bottom, side, back, front and any combination thereof.

According to another embodiment of the invention, a method as defined above is disclosed, additionally comprising a step of configuring the PTI to reduce the noise within the inner volume, in a predefined sound characteristic, and selecting the sound characteristic from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

According to another embodiment of the invention, a method as defined above is disclosed, additionally comprising a step of selecting at least one noise parameter to be reduced from a group consisting of: sound level reduction, sound reflections reduction, sound reverberation reduction, sound diffusion, altered sound signature, and any combination thereof.

According to another embodiment of the invention, a method as defined above is disclosed, additionally comprising a step of selecting at least one sound characteristic reaching the inner volume from the environment from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof, thereby generating at least one sound signature, to be changed by the PTI.

According to another embodiment of the invention, a method as defined above is disclosed, additionally comprising a step of selecting the sound signature from a group consisting of: configurable by the user, predefined, automatically adjustable in reference to the patient's life parameters, and any combination thereof.

According to another embodiment of the invention, a method as defined above is disclosed, additionally comprising a step of including at least one means selected from a group consisting of: a sound absorptive material, a resonator, a sound shield, a bass trap, a sound baffle, a diffuser, an insulation padding, a sound reflector, a sound muffler, and any combination thereof, configured to changing the sound signature reaching the patient.

According to another embodiment of the invention, a method as defined above is disclosed, additionally comprising a step of forming at least a portion of the envelope of a material selected from a group consisting of: at least one sealing material, at least one sound absorbent material, at least one vibration absorbing material, and any combination thereof.

According to another embodiment of the invention, a method as defined above is disclosed, additionally comprising a step of forming at least a portion of the envelope comprising n layers; further wherein each of the n layers comprising an inner side towards the inner volume, and an opposite outer side facing towards the environment.

According to another embodiment of the invention, a method as defined above is disclosed, additionally comprising a step of forming each of the n layers comprising a predefined Noise Reduction Coefficient (NRC) value, Sound Transmission Class (STC) value, or both; further wherein the NRC value, STC value, or both, can be equal or different for the each of one of n layers.

According to another embodiment of the invention, a method as defined above is disclosed, additionally comprising a step of forming the n layers comprising a Noise Reduction Coefficient (NRC) value for each of the n layers; where each of the layers comprising at least one sound level $S_1$ [dB] measured on the layer outer side, and at least one first sound level $S_n$ [dB], measured on the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising a step of forming the n layers comprising a Sound transmission class (STC) value for each of the n layers; where each of the layers comprising at least one sound level $S_1$ [dB] measured on the layer outer side, and at least one first sound level $S_n$ [dB], measured the layer inner side, having a $dS_1$- . . . $dSn$, wherein dS of the PTI equals $S_1$-Sn, and $S_1$-Sn<$S_1$.

According to another embodiment of the invention, a method as defined above is disclosed, additionally comprising the following steps: (a) forming the envelope further comprising a space, $S_{1-n}$, between at least two the of n layers; (b) configuring at least one $STC_1$ (sound transmission class) value, measured for the layers $_{1-n}$; and, (c) connecting reversible mobilization means, connected to at least one of the n layers, configured to mobilizing at least one of the n layers, having a space $S_{1-n}$ between at least two of n layers such that a space $S_{1-n,a}$ and $STC_2$ value measured for the layers $_{1-n}$ are provided; where $S_{1-n}$<$S_{1n,a}$ and where $STC_1$<$STC_2$.

According to another embodiment of the invention, a method as defined above is disclosed, additionally comprising a step of configuring the envelope to reduce reverberation of sound, reflections of sound, or both within the inner volume, by means of at least one selected from a group consisting of; absorptive material, a sound baffle, a sound diffuser, a sound resonator, a sound shield, an active sound cancellation device and any combination thereof.

According to another embodiment of the invention, a method as defined above is disclosed, additionally comprising the following steps: (a) a step of forming the envelope further characterized by an elongated shape, having a main longitudinal axis with a proximal end and an opposite distal end; (b) connecting a temperature regulating vent (TRV) to the PTI in at least one of the ends; (c) configuring the TRV to stream air from the end towards the opposite end substantially along the axis; (d) configuring the envelope, by means of size and shape, to accommodate the patient in parallel to the axis; and, (e) selecting the TRV from a group consisting of at least one first venting module, at least one first heating/cooling module, at least one filter located adjacently to either the first venting module or the first heating/cooling module, at least one humidifying module and any combination thereof.

According to one embodiment of the present invention a standard of care protocol for MRI of patients, comprising steps of: (a) obtaining a PTI suitable for magnetic resonance imaging device (MRD) with an open bore, the incubator comprising an inner volume having a first set of dimensions, the inner volume is adapted by means of shape and size to accommodating at least a portion of the MRI-compatible neonate's cradle, the inner volume further is covered by an envelope having a second set of dimensions, adapted by shape and size to be temporarily introduced within the open bore; when at least a portion of the envelope comprises MRI-safe thermo-isolating and noise reducing foam, confining the compartment from its environment; (b) placing the patient into the MRI-compatible neonate's cradle; (c) at least partially accommodating the MRI-compatible neonate's cradle by the PTI enveloped inner volume; and, (d) introducing the PTI accommodating the MRI-compatible neonate's cradle into MRI open bore and imaging; wherein at least one of the following is held true: (a) the sound pressure measured inside the PTI does not exceed a maximum level of 60 dB; and the sound level in the inner volume of the PTI compartment would be at least 10 dB lower than the sound level outside this compartment; (b) the sound pressure measured inside the PTI does not exceed a maximum level of 45 dB; and the sound level in the inner volume of the PTI compartment would be at least 10 dB lower than the sound level outside this compartment; (c) the average value of salivary cortisol level index from noise derived stress of patient when utilizing the PTI during MRI is n times lower than the average the value during MRI; n is equal or greater than 1.05; (d) the average number of movements per minute of patient when utilizing the PTI during MRI is m times lower than the average number of movements per minute of the patient; m is equal or greater than 1.05; (e) the average number of MRI repetition number per patient is p times lower when utilizing the PTI than the average number of MRI repetitions during MRI of patients; p is equal or greater than 1.05; (f) the temperature of the inner volume of the MRI-compatible neonate's cradle, housed within the PTI, is at the most 2° C. different than the control temperature of 36° C.; (g) the $O_2$ concentration within the MRI-compatible neonate's cradle housed, within the PTI, does not fall below 30 vol. %, and does not exceed 40 vol. %; (h) the $CO_2$ concentration within the MRI-compatible neonate's cradle housed within the PTI does not exceed 4%; (i) the PTI will continue to be used safely in occurrence of a leakage of up to 200 ml deposited in the compartment of the PTI; (j) the PTI will remain stable when tilted 10° in normal use and when tilted 20° during transportation; (k) the PTI will not tip over when the force is 100 N or less; (l) the average number of patients' MRI related fall incidents when utilizing the PTI is r times lower than the average of patients' MRI related fall incidents; r is equal or greater than 1.05; (m) the average number of patient infections acquired that are MRI associated, when utilizing the PTI, is s times lower than the average number of infections acquired by patients that are MRI associated; s is equal or greater than 1.05; (n) the average number of MRI associated patient's health complications when utilizing the PTI is t times lower than the average number of patient's MRI associated health complications, t is equal or greater than 1.05; (o) the radiated electromagnetic fields in the inner volume of the PTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (p) the average number of excessive heating incidents and burn incidents in association with MRD is u times lower when utilizing the PTI; u is equal or greater than 1.05.

Reference is now made to FIG. 1A, schematically illustrating, in an out of scale manner, an embodiment of the invention. In this embodiment the patient transport incubator includes a cylindered shaped enclosure (100) having at least two parts. At least a portion of the envelope enclosure comprises a thickened MRI permeable, non-interfering, safe foam layer (20). The envelope has an opening (30) allowing for an opened and closed configuration of the incubator, wherein the opened configuration enables placement of the patient. The envelope further is comprised from at least a portion of transparent material (10) enabling view of at least part of the patient. The envelope further has openings (52-57) that permit passage through or connection of a plurality of equipment dedicated to maintain, monitor, and control the patient status and incubator status. This equipment includes devices dedicated for medical supporting, monitoring, lighting, heating, viewing, ventilating, etc. Connected to the envelope is sensing equipment of the physical properties of the transport incubator and the inner volume such as temperature, humidity, gas concentration, vibration, sound level, drift, structural integrity, open or closed configuration, etc. The transport incubator further harbors a user interface space (50) were the connections and pass-through elements are organized. The user interface may also include indicators (51) such as visible, auditable, and sensible that respond to data from the sensing equipment of the incubator, and of the patient. In this embodiment the user interface is located at the front of the infant transport incubator so it is accessible when the incubator is inside MRD open bore.

According to another embodiment of the invention, the PTI, having all means for standing all applied regulations, especially the following standards and sections thereof: ANSI/AAMI/IEC 60601-2-20:2009 medical electrical equipment—part 2-20: particular requirements for the basic safety and essential performance of infant transport incubators; and more specifically to section 201.3.201; air controlled transport incubator in which the air temperature is automatically controlled by an air temperature sensor close to a value set by the operator; 201.3.202 average temperature average of temperature readings taken at regular intervals at any specified point in the compartment achieved during steady temperature condition; 201.3.203 average transport incubator temperature average of the infant transport incubator temperature readings taken at regular intervals achieved during steady temperature condition; 201.3.204 baby controlled transport incubator air controlled transport incubator which has the additional capability of automatically controlling the incubator air temperature in order to maintain the temperature as measured by a skin temperature sensor according to the control temperature set by the operator note an infant transport incubator operating as a baby controlled incubator is a physiologic closed-loop controller as defined in IEC 60601-1-10.; 201.3.205 compartment environmentally-controlled enclosure intended to contain an infant and with transparent section(s) which allows for viewing of the infant; 201.3.206 control temperature, temperature selected at the temperature control; 201.3.207 infant patient up to the age of three months and a weight less than 10 kg; 201.3.208 infant transport incubator, transportable me equipment that is equipped with a compartment and a transportable electrical power source with the means to control the environment of the infant primarily by heated air within the compartment; 201.3.209 skin temperature, temperature of the skin of the infant at a point on which the skin temperature sensor is placed; 201.3.210 skin temperature sensor sensing device intended to measure the infant's skin temperature, all incorporated herein in its entirely as a reference.

Reference is now made to FIG. 1B, schematically illustrating, in an out of scale manner, a cross section view of an embodiment of the invention along the line of A in FIG. 1A. An infant transport incubator, configured in a cylindered embodiment (100), comprising an envelope fitted to accommodate patient. In this embodiment the envelope shape is concave, and defined to fit the overall shape of the patient head (21). This envelope is provided in a plurality of dimensions and shapes to accommodate different needs: different patient sizes, providing a movement restricting space, ergonomic placement, a placement for the patient body arranged so it does not form conducting loops, fitting specific patient body position, etc.

Reference is now made to FIG. 2A, schematically illustrating, in an out of scale manner, an embodiment of the invention in a rectangular form (100). In this embodiment the patient transport incubator is connected to a detachable multi-use user interface module (80) whereas the rest of the envelope is disposable.

Reference is now made to FIG. 2B, schematically illustrating, in an out of scale manner, a cross section view of an embodiment of the invention along the line of A in FIG. 2A, showing a solid MRI safe foam layer (20), a partly concave envelope shape (21) and a transparent portion of the envelope (10).

Reference is now made to FIG. 2C, schematically illustrating, in an out of scale manner, an embodiment of the invention of a detachable user interface (80), harboring a handle for easy placement (81). In this embodiment the user interface includes: connections to medical and sensing devices (59), pass-through elements (52) for tubes (200), wires, etc., CPU (54) integrating analyzing and transmitting the data received from medical and sensing equipment, control unit of set equipment (53), indicators (51) for the data received from sensing and medical equipment and from CPU (54), power supply (58) that is internally supplied DC, externally supplied AC or DC or both, an alarm system harboring indicators (visual, audible, sensible).

Figure 2D:
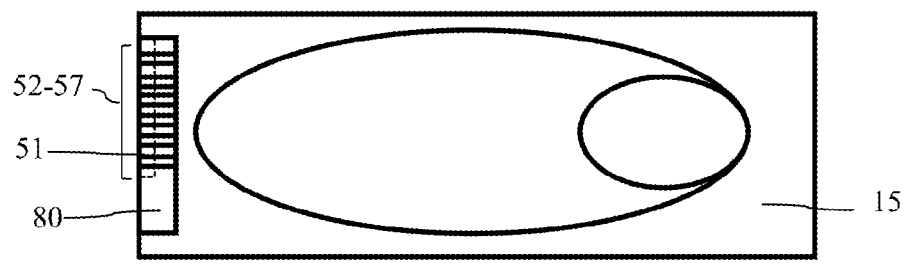
FIG. 2D is a schematic illustration of a cross section view of an infant transport incubator (100) in a rectangular embodiment, along the line of C in FIG. 2.

Reference is now made to FIG. 2D, schematically illustrating, in an out of scale manner, a cross section view of a rectangular embodiment (100) of the invention, along the line of C in FIG. 2, describing another embodiment of a partly concaved envelope formed in an ergonomic shape (15).

Figure 2E:
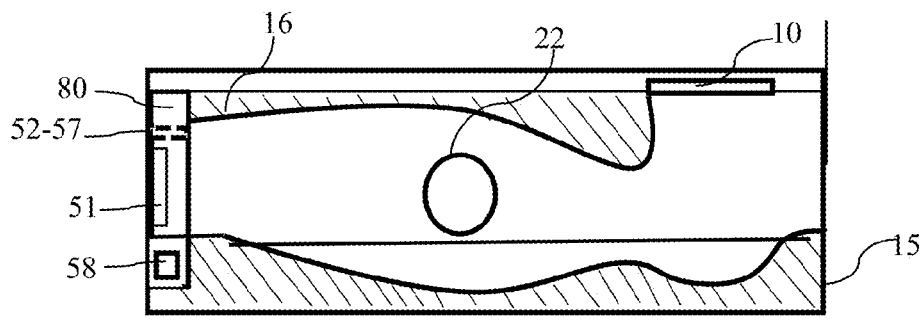
FIG. 2E is a schematic illustration of a cross section view of an infant transport incubator (100) in a rectangular embodiment, along the line of D in FIG. 2.

Reference is now made to FIG. 2E, schematically illustrating, in an out of scale manner, a cross section view of a rectangular embodiment (100) of the invention, along the line of D in FIG. 2, presenting the arrangement of an embodiment of the incubator in a multilayer construction. A module of user interface (80) is interconnected to the front side of envelope. The envelope includes thermo-isolating MRI safe, preamble, foam adapted to fit patient ergonomically constructed of two parts: top (16) and bottom (15). Further envelope harbors another opening (22) for passage of equipment such as medical equipment, sensing equipment, etc, and a transparent portion (10).

Figure 3:
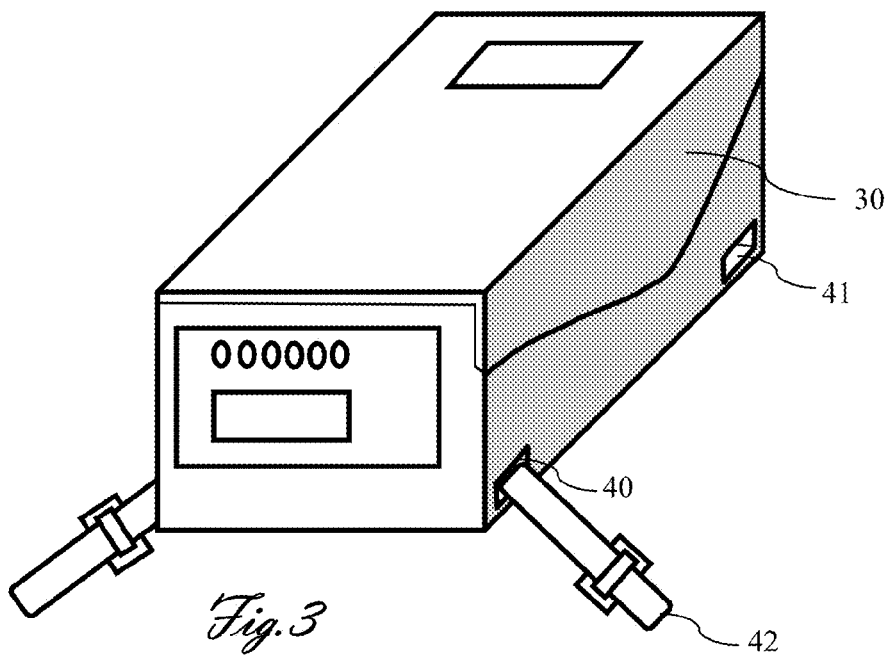
FIG. 3 is a schematic illustration of another embodiment of a PTI (100) that includes another embodiment of an opening (30), and attaching mechanism (42)

Reference is now made to FIG. 3, schematically illustrating, in an out of scale manner, an embodiment of the invention. A patient transport incubator (100) that includes another embodiment of an opening (30), and an attaching mechanism (42) that connect the PTI to the placement of the patient in the MRD bore. The attaching mechanism connects to a designated location in the incubator (40-41) on one side, the MRD on the other side.

Reference is now made to FIG. 4A, schematically illustrating, in an out of scale manner, an embodiment of the invention. A PTI in a cylindered embodiment (100) described as constructed of a top part (60) and bottom part (70) whereas each part is cast in one piece, and assembled together with a user interface (50) module (80). The top and bottom parts can be configured to have an opened or closed configuration further secured by a lock apparatus (90) so that the incubator does not change configuration due to patient's movements. Further this secure mechanism includes a fast release mechanism. This fast release mechanism provides immediate access to the patient in case of need.

Figure 4:
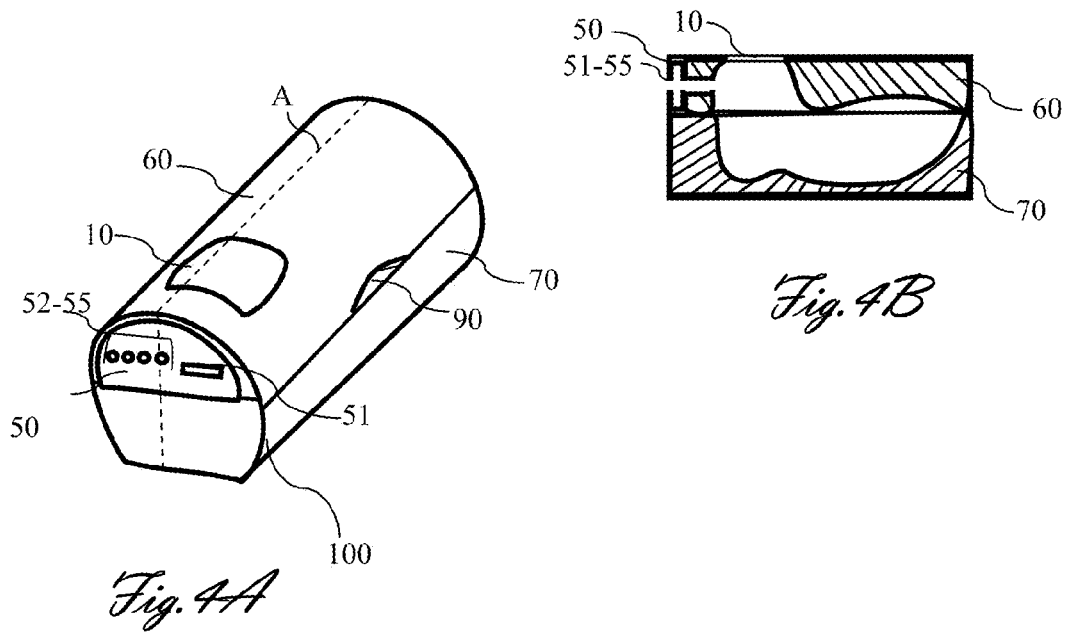
FIG. 4A is a schematic illustration of another exemplary cylindrical embodiment arrangement of a PTI (100)
FIG. 4B is a schematic illustration of a cross section view of a PTI (100) in cylindrical embodiment, along the line of A in FIG. 4.

Reference is now made to FIG. 4B, schematically illustrating, in an out of scale manner, a cross section view of a cylindrical embodiment (100) of the invention, along the line of A in FIG. 4, describing the arrangement of the incubator embodied in FIG. 4A.

Figure 5:
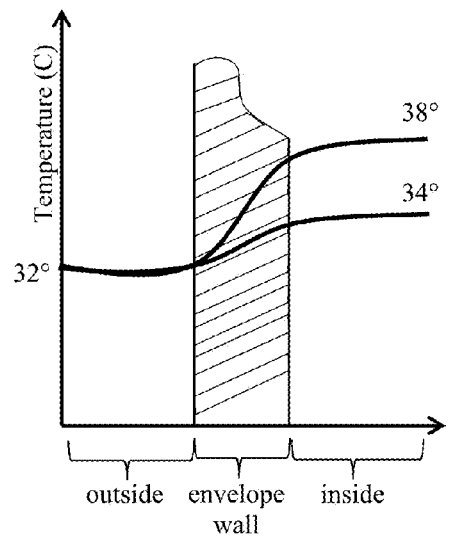
FIG. 5 is a schematic diagram demonstrating the temperature across one section of the envelope of a PTI.

Reference is made to FIG. 5. A schematic diagram illustrating, in an out of scale manner, the temperature measured across one section of the envelope of infant transport incubator, demonstrating the temperature inside the envelope is higher than the temperature measured on the outside.

Figure 6:
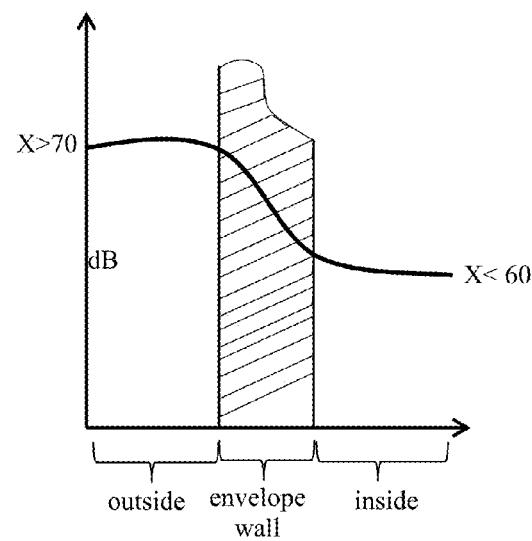
FIG. 6 is a schematic diagram demonstrating the sound level across one section of the envelope of the PTI.

Reference is made to FIG. 6. A schematic diagram illustrating, in an out of scale manner, the sound level across one section of the envelope of infant transport incubator, demonstrating that the sound levels within inner volume are lower than the sound levels outside the envelope.

Figure 7:
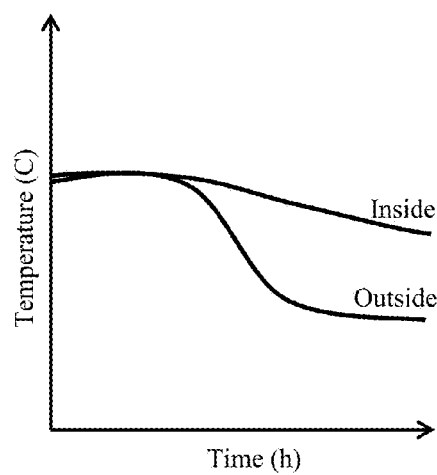
FIG. 7 is a schematic diagram demonstrating the temperature as a function of time within the envelope of a PTI, and on the outside.

Reference is made to FIG. 7. A schematic diagram illustrating, in an out of scale manner, the temperature as a function of time at an axis of a cross section of the foamed envelope. The temperature is measured both within the envelope of infant transport incubator, and outside the envelope. This diagram demonstrates that the change of the outside temperature does not reflect to the same extent on the temperature of the incubator's inner volume.

Figure 8:
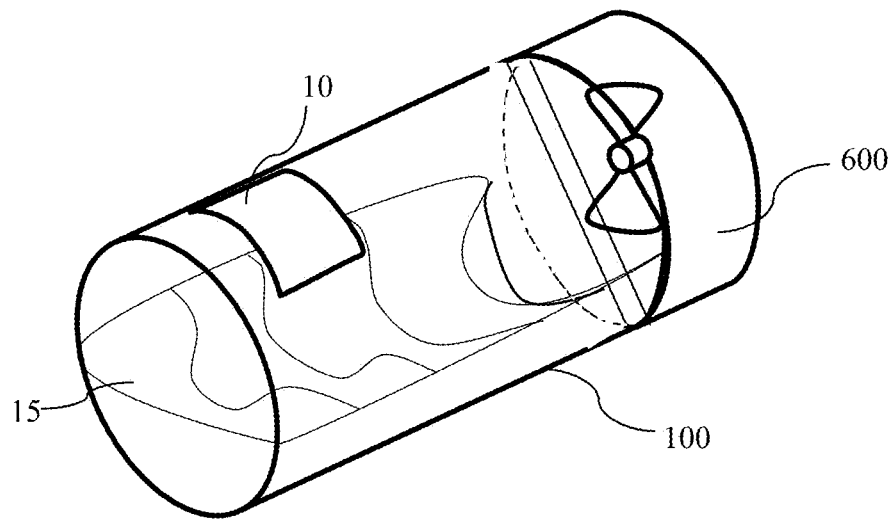
FIG. 8 is a schematic illustration of a PTI (100) in cylindrical embodiment, including a temperature regulating vent (600)

Reference is now made to FIG. 8, schematically illustrating, in an out of scale manner, an embodiment of the invention. In this embodiment the PTI (100) in an elongated configuration, is connected to a thermo-regulating vent (600) at one end. The PTI further includes a disposable foam mattress (15) and a transparent portion enabling patient view (10).

Figure 9:
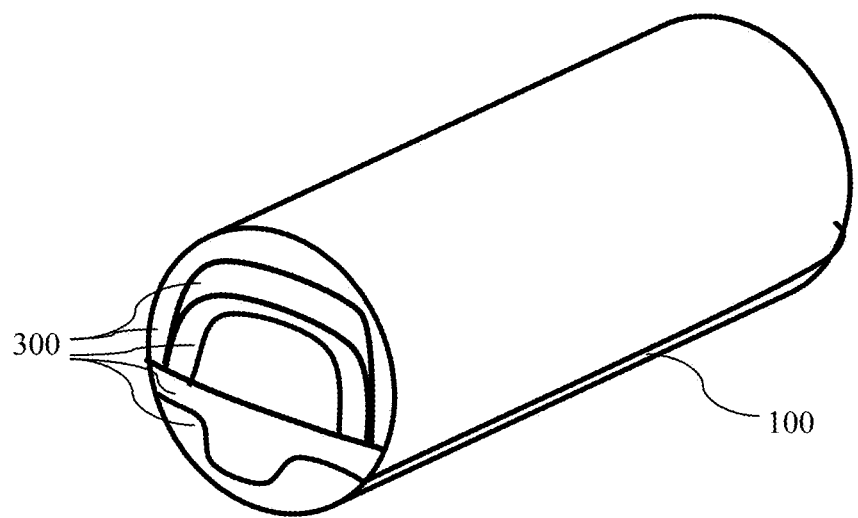
FIG. 9 is a schematic illustration of a PTI (100) in cylindrical embodiment, including a multilayered construction (300)

Reference is now made to FIG. 9, schematically illustrating, in an out of scale manner, an embodiment of the invention. In this embodiment the PTI (100) in an elongated configuration, comprising a multi-layered construction (300). Additionally or alternatively, the layers are of the same or different shape, width, length, size, material NRC, STC, noise absorption, thermal conductivity, thermal capacity, sound refractive quality, and etc.

Figure 10:
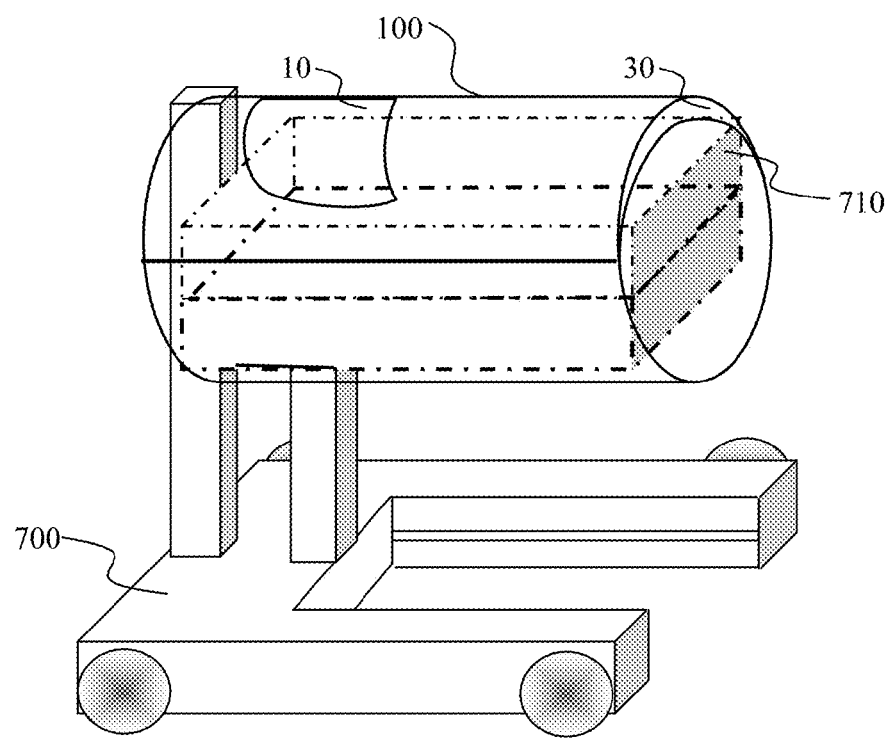
FIG. 10 is a schematic illustration of a PTI (100) in a cylindrical embodiment encapsulating an neonate incubator attached to an MRI cart; and, FIG. 11 is a schematic illustration of a PTI (100) in a canopy embodiment encapsulating a neonate incubator attached to an MRI cart.

Reference is now made to FIG. 10, schematically illustrating, in an out of scale manner, an embodiment of the invention. In this cylindered embodiment (100), the PTI's inner volume is adapted to fit, by means of size and shape, a MRI safe neonate incubator (710). Further in this embodiment the neonate incubator is attached to a MRI cart (700), while the assembly of the PTI encapsulating the infant incubator is designed to fit within the MRD open bore. At least a portion of the envelope enclosing the inner volume is made of thermo-regulating foam. This envelope has an opening (30), providing rapid, one step access to the incubator inside. At least a portion of the envelope is made of transparent material (10) enabling view of at least a part of neonate placed within.

Figure 11:
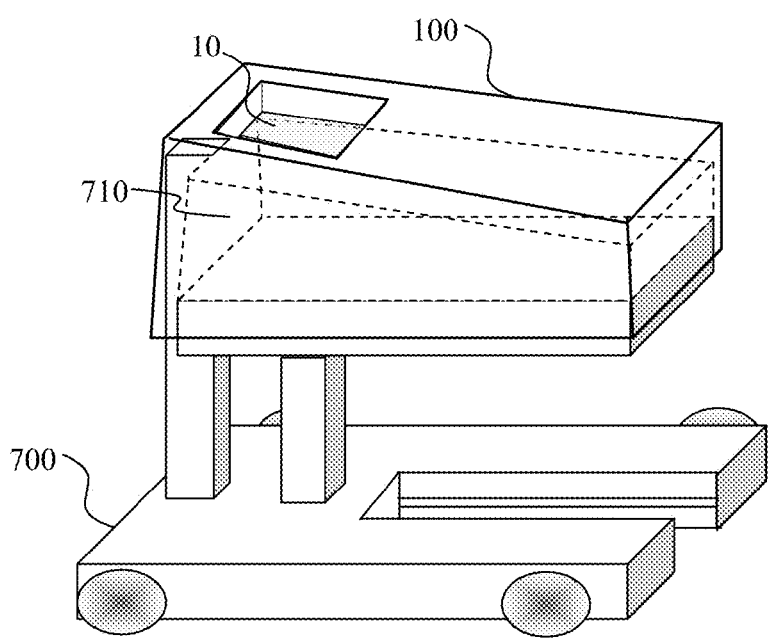

Reference is now made to FIG. 11, schematically illustrating, in an out of scale manner, an embodiment of the invention. In this embodiment the PTI (100) is configured to cover an infant incubator (710) attached to an MRI cart (700), as a canopy. Additionally, this canopy includes a transparent portion (10) enabling view of at least a part of the infant.

The invention claimed is:

1. A patient transport incubator (PTI) suitable for Magnetic Resonance Imaging (MRI) device, the MRI device having an open bore;
said PTI comprises:
an inner volume having a first set of dimension, said first set of dimensions including shape and size that are configured to accommodate a patient, said inner volume is further covered by an envelope having a second set of dimensions, said second set of dimensions including shape and size that are configured to be temporarily introduced within said open bore, wherein at least a portion of said envelope comprises MRI safe thermo-isolating and noise reducing foam; and
a first end and a second end, the first end comprises a detachable interface comprising:
i) a plurality of openings for passing through elements between an environment external to said MRI device and the inner volume,
ii) at least one indicator facing the environment external to said MRI device, and
iii) at least one computer processing unit (CPU) configured to transmit data to the at least one indicator;
wherein said PTI is configured to be inserted into said open bore of said MRI device.

2. The PTI of claim 1, wherein said envelope is configured for at least one open position for accommodating said patient, and at least one closed position configured to at least partially confine said patient within said inner volume.

3. The PTI of claim 1, wherein said envelope is configured to separate said patient tissues from coming into contact with said Magnetic Resonance Imaging (MRI) bore.

4. The PTI of claim 1, further comprising at least one sensor configured to sense at least one parameter selected from a group consisting of: temperature, humidity, $O_2$ concentration, $CO_2$ concentration, $O_2$ concentration, sound level, sound frequency, sound direction, sound amplitude, sound tone, sound speed, vibration, movement, drift, light, PTI configuration, PTI structural integrity, PTI lock configuration and any combination thereof.

5. The PTI of claim 1, wherein said envelope is configured to house at least one reversibly connectable module selected from a group consisting of: a temperature regulating vent module, a venting module, at least one life support system module, a monitoring module, a sensor module, and any combination thereof.

6. The PTI of claim 1, wherein said PTI is configured to change at least one sound characteristic reaching said inner volume from an environment, selected from a group consisting of: sound levels, tone, overtone composition, reverberations, sound frequency, sound wavelength, sound wave amplitude, sound wave speed, sound wave direction, sound wave energy, sound wave phase, sound wave shape, sound wave envelope, sound timbre, and any combination thereof.

7. The PTI of claim 1, wherein at least a portion of said envelope comprises n layers; further wherein each of said n layers comprises an inner side facing towards said inner volume, and an opposite outer side facing towards said environment; further wherein each of said n layers comprises a predefined Noise Reduction Coefficient (NRC) value, Sound Transmission Class (STC) value, or both; further wherein said NRC value, STC value, or both, can be equal or different for said each of one of n layers.

8. The PTI of claim 7, wherein each of said layers comprising at least one sound level $S_1$ [dB] measured on said layer outer side, and at least one first sound level $S_n$ [dB], measured on said layer inner side, having a $dS_1$ to $dSn$, wherein dS of said PTI equals $S_1$-Sn, and $S_1$-Sn<$S_1$.

9. The PTI of claim 1, having an elongated shape, having a main longitudinal axis with a proximal end and an opposite distal end; said PTI further comprising in at least one of said ends, a temperature regulating vent (TRV); said TRV is adapted to stream air from said end towards said opposite end substantially along the axis; and is configured, by means of size and shape, to accommodate said patient in parallel to the axis; further wherein said TRV is a module selected from a group consisting of at least one first venting module, at least one first heating/cooling module, at least one filter located adjacently to either said first venting module or said first heating/cooling module, at least one humidifying module and any combination thereof.

10. The PTI of claim 1, wherein said envelope shape is selected from a group consisting of: patient ergonomic, non-ergonomic, patient movement restrictive shape, and any combination thereof.

11. A method of magnetic resonance imaging of patients comprising steps of:
   a. obtaining a patient transport incubator (PTI) suitable for Magnetic Resonance Imaging (MRI) device, the MRI device having an open bore, wherein said PTI comprising:
   an inner volume having a first set of dimension, said first set of dimensions including shape and size that are configured to accommodate a patient, said inner volume is further covered by an envelope having a second set of dimensions, said second set of dimensions including shape and size that are configured to be temporarily introduced within said open bore, wherein at least a portion of said envelope comprises MRI safe thermo-isolating and noise reducing foam; and
   a first end and a second end, the first end comprises a detachable interface comprising:
   i) a plurality of openings for passing through elements between an environment external to said MRI device and the inner volume,
   ii) at least one indicator facing the environment external to said MRI device, and
   iii) at least one computer processing unit (CPU) configured to transmit data to the at least one indicator;
   b. placing said patient into an enveloped inner volume; and,
   c. inserting said PTI into said open bore and imaging the patient using the MRI device.

* * * * *